US006992761B2

(12) United States Patent  
Modlin et al.

(10) Patent No.: US 6,992,761 B2  
(45) Date of Patent: Jan. 31, 2006

(54) BROAD RANGE LIGHT DETECTION SYSTEM

(75) Inventors: Douglas N. Modlin, Palo Alto, CA (US); David P. Stumbo, Belmont, CA (US); Rick V. Stellmacher, San Jose, CA (US); Jonathan F. Petersen, Redwood City, CA (US); Todd E. French, Mountain View, CA (US)

(73) Assignee: Molecular Devices Corporation, Sunnyvale, CA (US)

( * ) Notice: Subject to any disclaimer, the term of this patent is extended or adjusted under 35 U.S.C. 154(b) by 295 days.

(21) Appl. No.: 10/445,292

(22) Filed: May 22, 2003

(65) Prior Publication Data

US 2004/0239922 A1    Dec. 2, 2004

Related U.S. Application Data

(60) Continuation-in-part of application No. 10/218,897, filed on Aug. 13, 2002, which is a continuation-in-part of application No. 10/041,532, filed on Jan. 7, 2002, now abandoned, and a continuation-in-part of application No. 10/012,255, filed on Nov. 12, 2001, (Continued)

(51) Int. Cl.
  *G01J 3/30* (2006.01)
  *G01N 21/54* (2006.01)
(52) U.S. Cl. .................... 356/317; 356/417; 250/458.1
(58) Field of Classification Search ................ 356/306, 356/317, 318, 319, 326, 328, 417; 250/458.1, 250/459.1, 461.1, 461.2

See application file for complete search history.

(56) References Cited

U.S. PATENT DOCUMENTS 2,719,214 A    9/1955   Potter
3,013,467 A   12/1961   Minsky
3,423,581 A    1/1969   Baer (Continued)

FOREIGN PATENT DOCUMENTS

EP    0 222 341 A1    5/1987
EP    0 266 881 A2    5/1988

(Continued)

OTHER PUBLICATIONS

*Standard Handbook for Electrical Engineers*, Fink et al., pp. 22-2 through 25-5 (11$^{th}$ ed. 1978).

(Continued)

*Primary Examiner*—F. L. Evans
(74) *Attorney, Agent, or Firm*—Kolisch Hartwell, P.C.

(57) ABSTRACT

Broad-range light-detection systems, including components and methods of use thereof. These systems may include apparatus and methods for detecting light with increased speed and/or detection efficiency, particularly in applications involving repeated analysis of the same sample and/or successive analysis of different samples, and particularly when the sample or samples have a wide range of light intensities. These systems also may include apparatus and methods for detecting light with increased accuracy over a broad range of intensities. These systems also may include vapparatus and methods for automatically scaling detection range to improve detection based on the intensity of the detected light.

46 Claims, 14 Drawing Sheets

Related U.S. Application Data now abandoned, and a continuation-in-part of application No. 10/004,647, filed on Dec. 3, 2001, now Pat. No. 6,498,335, and a continuation-in-part of application No. 09/836,575, filed on Apr. 16, 2001, now abandoned, and a continuation-in-part of application No. 09/778,224, filed on Feb. 6, 2001, now Pat. No. 6,838,051, and a continuation-in-part of application No. 09/767,434, filed on Jan. 22, 2001, now Pat. No. 6,486,947, and a continuation-in-part of application No. 09/765,869, filed on Jan. 19, 2001, now Pat. No. 6,466,316, and a continuation-in-part of application No. 09/759,711, filed on Jan. 12, 2001, now abandoned, and a continuation-in-part of application No. 09/733,370, filed on Dec. 8, 2000, now abandoned, and a continuation-in-part of application No. 09/710,061, filed on Nov. 10, 2000, now Pat. No. 6,825,921, and a continuation-in-part of application No. 09/629,599, filed on Jul. 31, 2000, now Pat. No. 6,469,311, and a continuation-in-part of application No. 09/478,819, filed on Jan. 5, 2000, now Pat. No. 6,488,892, and a continuation-in-part of application No. 09/349,733, filed on Jul. 8, 1999, now abandoned, and a continuation-in-part of application No. 09/302,158, filed on Apr. 29, 1999, now Pat. No. 6,576,476, and a continuation-in-part of application No. 09/144,578, filed on Aug. 31, 1998, now Pat. No. 6,499,366, said application No. 09/144,578 is a continuation of application No. 09/118,341, filed on Jul. 16, 1998, now Pat. No. 6,025,985, and a continuation of application No. 09/118,310, filed on Jul. 16, 1998, now Pat. No. 6,033,100, and a continuation of application No. 09/118,141, filed on Jul. 16, 1998, now Pat. No. 6,313,960, and a continuation of application No. PCT/US98/14575, filed on Jul. 15, 1998, now abandoned, and a continuation of application No. 09/062,472, filed on Apr. 17, 1998, now Pat. No. 6,071,748, said application No. 09/302,158 is a division of application No. 09/146,081, filed on Sep. 2, 1998, now Pat. No. 6,187,267, and a continuation of application No. 09/144,578, filed on Aug. 31, 1998, now Pat. No. 6,499,366, and a continuation of application No. 09/144,575, filed on Aug. 31, 1998, now Pat. No. 6,159,425, and a continuation of application No. 09/118,341, filed on Jul. 16, 1998, now Pat. No. 6,025,985, and a continuation of application No. 09/118,310, filed on Jul. 16, 1998, now Pat. No. 6,033,100, and a continuation of application No. 09/118,141, filed on Jul. 16, 1998, now Pat. No. 6,313,960, and a continuation of application No. PCT/US98/14575, filed on Jul. 15, 1998, now abandoned, and a continuation of application No. 09/062,472, filed on Apr. 17, 1998, now Pat. No. 6,071,748, said application No. 09/349,733 is a continuation of application No. PCT/US99/08410, filed on Apr. 16, 1999, now abandoned, and a continuation of application No. PCT/US99/03678, filed on Feb. 19, 1999, now abandoned, and a continuation of application No. PCT/US99/01656, filed on Jan. 25, 1999, now abandoned, and a continuation of application No. PCT/US98/23095, filed on Oct. 30, 1998, now abandoned, and a continuation of application No. 09/160,533, filed on Sep. 24, 1998, now Pat. No. 6,097,025, and a continuation of application No. 09/156,318, filed on Sep. 18, 1998, now Pat. No. 6,258,326, and a continuation of application No. 09/062,472, filed on Apr. 17, 1998, now Pat. No. 6,071,748, said application No. 09/478,819 is a continuation of application No. PCT/US99/08410, filed on Apr. 16, 1999, now abandoned, which is a continuation of application No. 09/160,533, filed on Sep. 24, 1998, now Pat. No. 6,097,025, and a continuation of application No. 09/156,318, filed on Sep. 18, 1998, now Pat. No. 6,258,326, and a continuation of application No. 09/062,472, filed on Apr. 17, 1998, now Pat. No. 6,071,748, said application No. 09/629,599 is a continuation of application No. 09/160,533, filed on Sep. 24, 1998, now Pat. No. 6,097,025, which is a continuation of application No. 09/478,819, filed on Jan. 5, 2000, now Pat. No. 6,488,892, and a continuation of application No. 09/156,318, filed on Sep. 18, 1998, now Pat. No. 6,258,326, and a continuation of application No. 09/146,081, filed on Sep. 2, 1998, now Pat. No. 6,187,267, and a continuation of application No. 09/144,578, filed on Aug. 31, 1998, now Pat. No. 6,499,366, and a continuation of application No. 09/144,575, filed on Aug. 31, 1998, now Pat. No. 6,159,425, and a continuation of application No. 09/118,341, filed on Jul. 16, 1998, now Pat. No. 6,025,985, and a continuation of application No. 09/118,310, filed on Jul. 16, 1998, now Pat. No. 6,033,100, and a continuation of application No. 09/118,141, filed on Jul. 16, 1998, now Pat. No. 6,313,960, and a continuation of application No. PCT/US98/14575, filed on Jul. 15, 1998, now abandoned, said application No. 09/733,370 is a continuation of application No. 09/144,575, filed on Aug. 31, 1998, now Pat. No. 6,159,425, which is a continuation of application No. 09/118,341, filed on Jul. 16, 1998, now Pat. No. 6,025,985, and a continuation of application No. 09/118,310, filed on Jul. 16, 1998, now Pat. No. 6,033,100, and a continuation of application No. 09/118,141, filed on Jul. 16, 1998, now Pat. No. 6,313,960, and a continuation of application No. PCT/US98/14575, filed on Jul. 15, 1998, now abandoned, and a continuation of application No. 09/062,472, filed on Apr. 17, 1998, now Pat. No. 6,071,748, said application No. 09/759,711 is a continuation of application No. PCT/US99/16057, filed on Jul. 15, 1999, now abandoned, which is a continuation of application No. 09/160,533, filed on Sep. 24, 1998, now Pat. No. 6,097,025, and a continuation of application No. PCT/US98/14575, filed on Jul. 15, 1998, now abandoned, said application No. 09/765,869 is a continuation of application No. PCT/US99/16621, filed on Jul. 23, 1999, now abandoned, said application No. 09/767,434 is a continuation of application No. PCT/US99/16453, filed on Jul. 21, 1999, said application No. 09/778,224 is a continuation of application No. 09/777,343, filed on Feb. 5, 2001, now Pat. No. 6,902,703, which is a continuation of application No. PCT/US00/12277, filed on May 3, 2000, now abandoned, said application No. 10/004,647 is a continuation of application No. 09/643,221, filed on Aug. 18, 2000, now Pat. No. 6,326,605, which is a continuation of application No. PCT/US99/03678, filed on Feb. 19, 1999, and a continuation of application No. PCT/US99/01656, filed on Jan. 25, 1999, now abandoned, and a continuation of application No. PCT/US98/23095, filed on Oct. 30, 1998, now abandoned, and a continuation of application No. 09/062,472, filed on Apr. 17, 1998, now Pat. No. 6,071,748, and a continuation of application No. 09/160,533, filed on Sep. 24, 1998, now Pat. No. 6,097,025, said application No. 10/012,255 is a continuation-in-part of application No. 09/770,720, filed on Jan. 25, 2001, now abandoned, and a continuation-in-part of application No. 09/767,579, filed on Jan. 22, 2001, now Pat. No. 6,317,207, and a continuation-in-part of application No. 09/767,316, filed on Jan. 22, 2001, now Pat. No. 6,503,719, and a continuation-in-part of application No. 09/766,131, filed on Jan. 19, 2001, now abandoned, and a continuation-in-part of application No. 09/765,874, filed on Jan. 19, 2001, now Pat. No. 6,483,582, and a continuation-in-part of application No. 09/722,247, filed on Nov. 24, 2000, now abandoned, and a continuation-in-part of application No. 09/626,208, filed on Jul. 26, 2000, now abandoned, said application No. 09/626,208 is a continuation of application No. PCT/US99/01656, filed on Jan. 25, 1999, now abandoned, which is a continuation-in-part of application No. PCT/US98/23095, filed on Oct. 30, 1998, now abandoned, and a continuation-in-part of application No. 09/160,533, filed on Sep. 24, 1998, now Pat. No. 6,097,025, and a continuation-in-part of application No. 09/062,472, filed on Apr. 17, 1998, now Pat. No. 6,071,748, said application No. 09/766,131 is a continuation of application No. PCT/US99/16286, filed on Jul. 26, 1999, now abandoned, said application No. 09/765,874 is a continuation of application No. PCT/US99/16287, filed on Jul. 26, 1999, now abandoned, said application No. 09/767,316 is a continuation of application No. PCT/US00/00895, filed on Jan. 14, 2000, now abandoned, said application No. 09/767,579 is a continuation of application No. PCT/US00/04543, filed on Feb. 22, 2000, now abandoned, said application No. 09/770,720 is a continuation of application No. PCT/US00/06841, filed on Mar. 15, 2000, which is a continuation-in-part of application No. 09/494,407, filed on Jan. 28, 2000, now Pat. No. 6,297,018, and a continuation-in-part of application No. PCT/US00/00895, filed on Jan. 14, 2000, now abandoned, and a continuation-in-part of application No. 09/349,733, filed on Jul. 8, 1999, now abandoned, and a continuation-in-part of application No. PCT/US99/08410, filed on Apr. 16, 1999, now abandoned, said application No. 09/722,247 is a continuation-in-part of application No. 09/626,208, filed on Jul. 26, 2000, now abandoned, said application No. 10/041,532 is a continuation of application No. PCT/US00/18547, filed on Jul. 7, 2000, now abandoned.

(60) Provisional application No. 60/383,311, filed on May 22, 2002, provisional application No. 60/383,198, filed on May 22, 2002, provisional application No. 60/383,197, filed on May 22, 2002, provisional application No. 60/190,265, filed on Mar. 17, 2000, provisional application No. 60/184,924, filed on Feb. 25, 2000, provisional application No. 60/184,719, filed on Feb. 24, 2000, provisional application No. 60/182,419, filed on Feb. 14, 2000, provisional application No. 60/167,463, filed on Nov. 24, 1999, provisional application No. 60/167,301, filed on Nov. 24, 1999, provisional application No. 60/164,633, filed on Nov. 10, 1999, provisional application No. 60/153,251, filed on Sep. 10, 1999, provisional application No. 60/143,185, filed on Jul. 9, 1999, provisional application No. 60/142,721, filed on Jul. 7, 1999, provisional application No. 60/138,893, filed on Jun. 11, 1999, provisional application No. 60/138,737, filed on Jun. 11, 1999, provisional application No. 60/138,438, filed on Jun. 10, 1999, provisional application No. 60/138,311, filed on Jun. 9, 1999, provisional application No. 60/136,566, filed on May 28, 1999, provisional application No. 60/135,284, filed on May 21, 1999, provisional application No. 60/132,263, filed on May 3, 1999, provisional application No. 60/132,262, filed on May 3, 1999, provisional application No. 60/130,149, filed on Apr. 20, 1999, provisional application No. 60/126,661, filed on Mar. 29, 1999, provisional application No. 60/125,346, filed on Mar. 19, 1999, provisional application No. 60/124,686, filed on Mar. 16, 1999, provisional application No. 60/121,229, filed on Feb. 23, 1999, provisional application No. 60/119,884, filed on Feb. 12, 1999, provisional application No. 60/119,829, filed on Feb. 12, 1999, provisional application No. 60/117,278, filed on Jan. 26, 1999, provisional application No. 60/116,113, filed on Jan. 15, 1999, provisional application No. 60/114,209, filed on Dec. 29, 1998, provisional application No. 60/104,964, filed on Oct. 20, 1998, provisional application No. 60/100,951, filed on Sep. 18, 1998, provisional application No. 60/100,817, filed on Sep. 18, 1998, provisional application No. 60/094,306, filed on Jul. 27, 1998, provisional application No. 60/094,276, filed on Jul. 27, 1998, provisional application No. 60/094,275, filed on Jul. 27, 1998, provisional application No. 60/093,838, filed on Jul. 22, 1998, provisional application No. 60/093,768, filed on Jul. 22, 1998, provisional application No. 60/092,203, filed on Jul. 9, 1998, provisional application No. 60/089,848, filed on Jun. 19, 1998, provisional application No. 60/085,500, filed on May 14, 1998, provisional application No. 60/085,335, filed on May 13, 1998, provisional application No. 60/084,167, filed on May 4, 1998, provisional application No. 60/082,253, filed on Apr. 17, 1998, provisional application No. 60/075,806, filed on Feb. 24, 1998, provisional application No. 60/075,414, filed on Feb. 20, 1998, provisional application No. 60/072,780, filed on Jan. 27, 1998, provisional application No. 60/117,278, filed on Jan. 26, 1999, provisional application No. 60/072,449, filed on Jan. 26, 1998, provisional application No. 60/063,811, filed on Oct. 31, 1997, provisional application No. 60/059,639, filed on Sep. 20, 1997, provisional application No. 60/052,876, filed on Jul. 16, 1997.

(56) References Cited

U.S. PATENT DOCUMENTS

| | | |
|---|---|---|
| 3,516,736 A | 6/1970 | Weaver |
| 3,849,654 A | 11/1974 | Malvin |
| 3,885,162 A | 5/1975 | Geertz |
| 3,932,023 A | 1/1976 | Humer |
| 4,011,451 A | 3/1977 | Nelson |
| 4,033,697 A | 7/1977 | Pfoutz et al. |
| 4,067,653 A | 1/1978 | Fletcher et al. |
| 4,074,939 A | 2/1978 | Rabl |
| 4,076,420 A | 2/1978 | De Maeyer et al. |
| 4,100,416 A | 7/1978 | Hirschfeld |

| | | | | | |
|---|---|---|---|---|---|
| 4,144,452 A | 3/1979 | Harte | 5,289,407 A | 2/1994 | Strickler et al. |
| 4,150,870 A | 4/1979 | d'Auria | 5,307,144 A | 4/1994 | Hiroshi et al. |
| 4,203,670 A | 5/1980 | Bromberg | 5,315,015 A | 5/1994 | Hui et al. |
| 4,240,751 A | 12/1980 | Linnecke et al. | 5,317,485 A | 5/1994 | Merjanian |
| 4,296,326 A | 10/1981 | Haslop et al. | 5,319,436 A | 6/1994 | Manns et al. |
| 4,397,560 A | 8/1983 | Andresen | 5,323,008 A | 6/1994 | Studholme et al. |
| 4,451,149 A | 5/1984 | Noeller | 5,323,010 A | 6/1994 | Gratton et al. |
| 4,451,433 A | 5/1984 | Yamashita et al. | 5,340,716 A | 8/1994 | Ullman et al. |
| 4,485,430 A | 11/1984 | Achiaga Fustel | 5,340,747 A | 8/1994 | Eden |
| 4,501,970 A | 2/1985 | Nelson | 5,341,215 A | 8/1994 | Seher |
| 4,567,847 A | 2/1986 | Linner | 5,353,112 A | 10/1994 | Smith |
| 4,591,550 A | 5/1986 | Hafeman et al. | 5,355,215 A | 10/1994 | Schroeder et al. |
| 4,626,684 A | 12/1986 | Landa | 5,357,095 A | 10/1994 | Weyrauch et al. |
| 4,646,214 A | 2/1987 | Mendleski | 5,361,626 A | 11/1994 | Colligan et al. |
| 4,685,801 A | 8/1987 | Minekane | 5,384,093 A | 1/1995 | Ootani et al. |
| 4,699,512 A | 10/1987 | Koshi | 5,401,465 A | 3/1995 | Smethers et al. |
| 4,704,255 A | 11/1987 | Jolley | 5,418,371 A | 5/1995 | Aslund et al. |
| 4,707,067 A | 11/1987 | Haberland et al. | 5,420,408 A | 5/1995 | Weyrauch et al. |
| 4,730,921 A | 3/1988 | Klein et al. | 5,436,718 A | 7/1995 | Fernandes et al. |
| 4,737,464 A | 4/1988 | McConnell et al. | 5,445,935 A | 8/1995 | Royer |
| 4,738,825 A | 4/1988 | Kelln et al. | 5,449,921 A | 9/1995 | Baba |
| 4,741,619 A | 5/1988 | Humphries et al. | 5,457,527 A | 10/1995 | Manns et al. |
| 4,753,501 A | 6/1988 | Battle | 5,459,300 A | 10/1995 | Kasman |
| 4,758,786 A | 7/1988 | Hafeman | 5,480,804 A | 1/1996 | Niwa et al. |
| 4,762,420 A | 8/1988 | Bowley | 5,485,530 A | 1/1996 | Lakowicz et al. |
| 4,772,453 A | 9/1988 | Lisenbee | 5,487,872 A | 1/1996 | Hafeman et al. |
| 4,784,275 A | 11/1988 | Fridge | 5,491,343 A | 2/1996 | Brooker |
| 4,802,768 A | 2/1989 | Gifford et al. | 5,500,188 A | 3/1996 | Hafeman et al. |
| 4,808,828 A | 2/1989 | Kitamori et al. | 5,504,337 A | 4/1996 | Lakowicz et al. |
| 4,810,096 A | 3/1989 | Russell et al. | 5,512,492 A | 4/1996 | Herron et al. |
| 4,826,660 A | 5/1989 | Smith et al. | 5,523,573 A | 6/1996 | Hänninen et al. |
| 4,855,930 A | 8/1989 | Chao et al. | 5,527,684 A | 6/1996 | Mabile et al. |
| 4,868,103 A | 9/1989 | Stavrianopoulos et al. | 5,528,046 A | 6/1996 | Ishikawa |
| 4,873,633 A | 10/1989 | Mezei, Louis M. et al. | 5,537,343 A | 7/1996 | Kikinis et al. |
| 4,877,965 A | 10/1989 | Dandliker et al. | 5,541,113 A | 7/1996 | Siddigi et al. |
| 4,885,087 A | 12/1989 | Kopf | 5,542,012 A | 7/1996 | Fernandes et al. |
| 4,892,409 A | 1/1990 | Smith | 5,557,398 A | 9/1996 | Wechsler et al. |
| 4,897,548 A | 1/1990 | Döme et al. | 5,561,068 A | 10/1996 | Rounbehler et al. |
| 4,923,819 A | 5/1990 | Fernandez et al. | 5,589,136 A | 12/1996 | Northrup et al. |
| 4,931,402 A | 6/1990 | Abplanalp | 5,589,350 A | 12/1996 | Bochner |
| 4,936,682 A | 6/1990 | Hoyt | 5,589,351 A | 12/1996 | Harootunian |
| 4,948,442 A | 8/1990 | Manns | 5,592,289 A | 1/1997 | Norris |
| 4,963,815 A | 10/1990 | Hafeman | 5,593,867 A | 1/1997 | Walker et al. |
| 4,968,148 A | 11/1990 | Chow et al. | 5,595,710 A | 1/1997 | Van Dusen et al. |
| 4,979,821 A | 12/1990 | Schutt et al. | 5,599,500 A | 2/1997 | Jones |
| 5,001,725 A | 3/1991 | Senderowicz et al. | 5,604,130 A | 2/1997 | Warner et al. |
| 5,009,488 A | 4/1991 | Fay et al. | 5,620,894 A | 4/1997 | Barger et al. |
| 5,018,866 A | 5/1991 | Osten | 5,626,134 A | 5/1997 | Zuckerman |
| 5,020,995 A | 6/1991 | Levy | 5,631,734 A | 5/1997 | Stern et al. |
| 5,034,613 A | 7/1991 | Denk et al. | 5,633,724 A | 5/1997 | King et al. |
| 5,039,219 A | 8/1991 | James et al. | 5,635,402 A | 6/1997 | Alfano et al. |
| 5,047,215 A | 9/1991 | Manns | 5,641,633 A | 6/1997 | Linn et al. |
| 5,058,045 A | 10/1991 | Ma | 5,645,800 A | 7/1997 | Masterson et al. |
| 5,082,628 A | 1/1992 | Andreotti et al. | 5,663,545 A | 9/1997 | Marquiss |
| 5,084,246 A | 1/1992 | Lyman et al. | 5,670,113 A | 9/1997 | Akong et al. |
| 5,091,652 A | 2/1992 | Mathies et al. | 5,672,880 A | 9/1997 | Kain |
| 5,095,517 A | 3/1992 | Monguzzi et al. | 5,676,943 A | 10/1997 | Baetge et al. |
| 5,096,807 A | 3/1992 | Leaback | 5,677,196 A | 10/1997 | Herron et al. |
| 5,164,319 A | 11/1992 | Hafeman et al. | 5,679,310 A | 10/1997 | Manns |
| 5,169,601 A | 12/1992 | Ohta et al. | 5,736,410 A | 4/1998 | Zarling et al. |
| 5,192,510 A | 3/1993 | Zoha et al. | 5,738,825 A | 4/1998 | Rudigier et al. |
| 5,196,709 A | 3/1993 | Berndt et al. | 5,741,554 A | 4/1998 | Tisone |
| 5,198,670 A | 3/1993 | VanCauter et al. | 5,746,974 A | 5/1998 | Massey et al. |
| 5,206,568 A | 4/1993 | Björnson et al. | 5,750,410 A | 5/1998 | Dou et al. |
| 5,208,161 A | 5/1993 | Saunders et al. | 5,756,292 A | 5/1998 | Royer |
| 5,208,651 A | 5/1993 | Buican | 5,760,900 A | 6/1998 | Ito et al. .................... 356/338 |
| 5,216,488 A | 6/1993 | Tuunanen et al. | 5,766,875 A | 6/1998 | Hafeman et al. |
| 5,225,164 A | 7/1993 | Astle | 5,780,857 A | 7/1998 | Harju et al. |
| 5,257,202 A | 10/1993 | Feddersen et al. | 5,798,083 A | 8/1998 | Massey et al. |
| 5,270,788 A | 12/1993 | Cercek et al. | 5,798,085 A | 8/1998 | Seaton et al. |
| 5,273,718 A | 12/1993 | Sköld et al. | 5,825,617 A | 10/1998 | Kochis et al. |
| 5,275,951 A | 1/1994 | Chow et al. | 5,842,582 A | 12/1998 | DeStefano, Jr. |
| 5,281,825 A | 1/1994 | Berndt et al. | 5,888,454 A | 3/1999 | Leistner et al. |

| | | | |
|---|---|---|---|
| 5,905,571 | A | 5/1999 | Butler et al. |
| 5,920,389 | A * | 7/1999 | Bungo ..................... 356/325 |
| 5,933,232 | A | 8/1999 | Atzler et al. |
| 5,959,738 | A | 9/1999 | Hafeman et al. |
| 5,989,835 | A | 11/1999 | Dunlay et al. |
| 5,993,746 | A | 11/1999 | Priha et al. |
| 6,020,591 | A | 2/2000 | Harter et al. |
| 6,025,985 | A | 2/2000 | Leytes et al. |
| 6,033,100 | A | 3/2000 | Marquiss et al. |
| 6,071,748 | A | 6/2000 | Modlin et al. |
| 6,097,025 | A | 8/2000 | Modlin et al. |
| 6,137,584 | A | 10/2000 | Seidel et al. |
| 6,159,425 | A | 12/2000 | Edwards et al. |
| 6,187,267 | B1 | 2/2001 | Taylor et al. |
| 6,232,608 | B1 | 5/2001 | Giebeler et al. ......... 250/458.1 |
| 6,236,456 | B1 | 5/2001 | Giebeler et al. ............ 356/318 |
| 6,313,471 | B1 | 11/2001 | Giebeler et al. ......... 250/458.1 |
| 6,316,774 | B1 | 11/2001 | Giebeler et al. ......... 250/458.1 |

FOREIGN PATENT DOCUMENTS

| | | |
|---|---|---|
| EP | 0 259 386 B1 | 4/1991 |
| EP | 0 977 037 A1 | 2/2000 |
| EP | 0 993 916 A2 | 4/2000 |
| EP | 0 995 555 A1 | 4/2000 |
| EP | 1 003 020 A1 | 5/2000 |
| EP | 1 003 039 A1 | 5/2000 |
| GB | 2 215 838 A | 9/1989 |
| GB | 2 228 081 A | 8/1990 |
| WO | WO99/04288 | 1/1999 |
| WO | WO 99/08233 | 2/1999 |
| WO | WO99/23466 | 5/1999 |
| WO | WO99/37203 | 7/1999 |
| WO | WO99/42817 | 8/1999 |
| WO | WO99/54711 | 10/1999 |
| WO | WO00/04364 | 1/2000 |
| WO | WO00/06989 | 2/2000 |
| WO | WO00/06990 | 2/2000 |
| WO | WO00/06991 | 2/2000 |
| WO | WO00/42209 | 2/2000 |
| WO | WO 00/50877 | 8/2000 |
| WO | WO 00/55372 | 9/2000 |
| WO | WO 00/66269 | 11/2000 |
| WO | WO01/04608 | 1/2001 |

OTHER PUBLICATIONS

*Fundamentals of Light Microscopy*, Spencer, Cambridge University Press, 1982.
Joseph R. Lakowicz, *Principles of Fluorescence Spectroscopy*, First Edition, Sep. 1983.
*Basic Fluorescence Microscopy*, Taylor et al., *Methods in Cell Biology*, vol. 29, pp. 207-237, 1989.
*Quantitative Fluorescence Microscopy Using Photomultiplier Tubes and Imaging Detectors*, Wampler et al., *Methods in Cell Biology*, vol. 29, pp. 239-267, 1989.
*Three-Dimensional Confocal Fluorescence Microscopy*, Brakenhoff et al., *Methods in Cell Biology*, vol. 30, pp. 379-389, 1989.
*Laser Scanning Confocal Microscopy of Living Cells*, Lemasters et al., *Optical Microscopy: Emerging Methods and Applications*, pp. 339-345, 1993.
*Time-Resolved Fluorescence Lifetime Imaging*, vandeVen et al., *Optical Microscopy: Emerging Methods and Applications*, pp. 373-389, 1993.
*Electrochemiluminescence: A New Diagnostic and Research Tool*, Yang et al., *Bio/Technology*, vol. 12, pp. 193-194, Feb. 1994.
*Sorting Single Molecules: Application to Diagnostics and Evolutionary Biotechnology*, Eigen et al., *PNAS*, vol. 91, pp. 5740-5747, 1994.

*High Throughput Screening Using Dynamic Fluorescence*, Swift et al., *SPIE*, vol. 2388, pp. 182-189, Feb. 6-8, 1995.
Genesis Series Robotic Sample Processors brochure, Tecan AG, Oct. 1997.
Genesis Robotic Microplate Processor brochure, Tecan AG, Nov. 1997.
A Measure of Brilliance, TR717 Microplate Luminometer brochure, Tropix, Inc., 1997.
Advanced Microplate Dectection Systems brochure, Tecan AG, Feb. 1998.
The SPECTRA Family brochure, Tecan AG, Feb. 1998.
Assist Plate Handling Device brochure, Labsystems, May 1998.
Wallac Time-Resolved Fluorometry-The Key to Improved Assay Sensitivity, internet description pp., Jul. 7, 1998.
Wallac 1234 DELFIA Fluorometer, internet description page, Jul. 7, 1998.
Wallac 1420 VICTOR Multilabel Counter, internet description pages, Jul. 7, 1998.
Wallac 1420 VICTOR$^2$ Multilabel Counter, internet description pages, Jul. 7, 1998.
Wallac 1442 ARTHUR Multi-Wavelength Fluoroimager, internet description page, Jul. 7, 1998.
Wallac Labelling Reagents for Time-Resolved Fluorometry, internet description page, Jul. 7, 1998.
Genesis Assay Workstation brochure, Tecan AG, Jul. 1998.
Genesis Logistics Workstation brochure, Tecan AG, Jul. 1998.
Polarion brochure, Tecan AG, Aug. 1998.
CytoFluor Fluorescence Multi-Well Plate Reader brochure, PerSeptive Biosystems, 1998.
*Fixed Polarizer Ellipsometry for Simple and Sensitive Detection of Thin Films Generated by Specific Molecular Interactions: Applications in Immunoassays and DNA Sequence Detection*, Ostroff et al., *Clinical Chemistry*, vol. 44, No. 9, pp. 2031-2035, 1998.
Microplate Instrumentation Catalogue 1998, Labsystems, 1998.
Magellan, Instrument Control and Data Analysis Software brochure, Tecan AG, Nov. 1999.
TWISTER™, Tecan's Automated Microplate Handler brochure, Tecan AG, Nov. 1999.
*A Microfabricated Fluorescence-Activated Cell Sorter*, Fu et al., *Nature Biotechnology*, vol. 17, pp. 1109-1111, Nov. 1999.
Absorbance Readers brochure, Tecan AG, Dec. 1999.
ULTRA—The Solution for HTS and Assay Development brochure, Tecan Austria GmbH, Dec. 1999.
Joseph R. Lakowicz, *Principles of Fluorescence Spectroscopy*, Second Edition, 1999.
CyBi™-Lumax 1,536 brochure, CyBio AG, May 2000.
CyBi™-PlateSafe brochure, CyBio AG, May 2000.
SPECTRAmax® GEMINI XS brochure, Molecular Devices Corp., Jun. 2000.
Packard BioScience Company Introduces the Fusion™ Universal Microplate Analyzer press release, Packard BioScience Company, Jun. 29, 2000.
SPECTRAmax® PLUS$^{384}$ brochure, Molecular Devices Corp., Jun. 2000.
Labcyte: Research and Clinical Instruments for Life Sciences brochure, Arlena Research LLC, Aug. 1, 2000.

Fusion™, Universal Microplate Analyzer, Packard BioScience Company, Aug. 2000.

CyBi™-Screen-Machine: One System-Many Solutions brochure, CyBio AG, 2000.

Acumen Explorer brochure, Acumen, undated.

FLIPR 384: Essential Technology for Drug Discovery brochure, Molecular Devices Corp., undated.

FLUOstar Galaxy brochure, BMG Labtechnologies GmbH, undated.

NEPHELOstar Galaxy brochure, BMG Labtechnologies GmbH, undated.

LUMIstar Galaxy brochure, BMG Labtechnologies GmbH, undated.

POLARstar Galaxy brochure, BMG Labtechnologies GmbH, undated.

POLARstar Galaxy flyer, BMG Labtechnologies GmbH, undated.

* cited by examiner

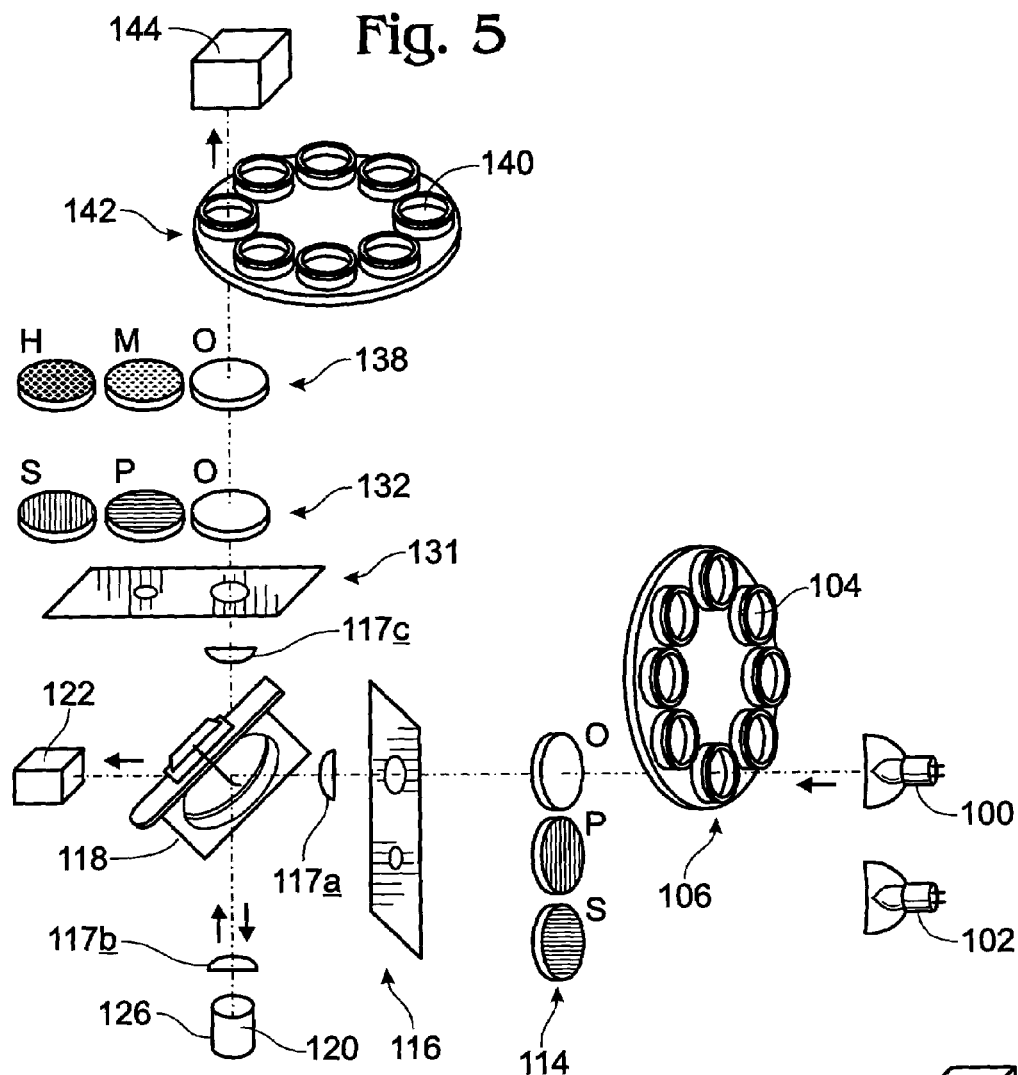
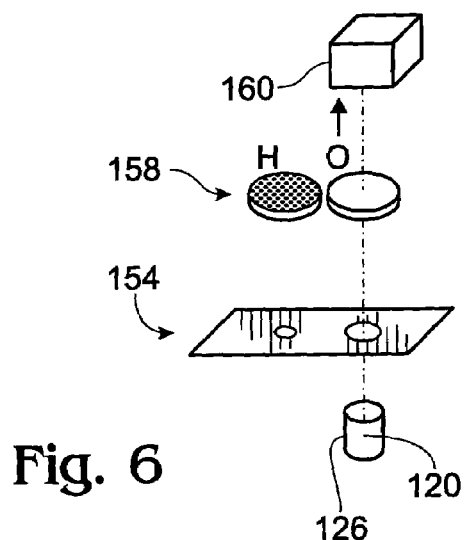

BROAD RANGE LIGHT DETECTION SYSTEM

CROSS-REFERENCES TO PRIORITY APPLICATIONS

This application is a continuation-in-part of U.S. patent application Ser. No. 10/218,897, filed Aug. 13, 2002. This application also is based upon and claims benefit under 35 U.S.C. § 119(e) of the following U.S. provisional patent applications: Ser. No. 60/383,197, filed May 22, 2002; Ser. No. 60/383,198, filed May 22, 2002; and Ser. No. 60/383,311, filed May 22, 2002.

U.S. patent application Ser. No. 10/218,897, in turn, is a continuation-in-part of the following U.S. patent applications: Ser. No. 09/144,578, filed Aug. 31, 1998 now U.S. Pat. No. 6,499,366; Ser. No. 09/302,158, filed Apr. 29, 1999 now U.S. Pat. No. 6,576,476; Ser. No. 09/349,733, filed Jul. 8, 1999, now abandoned; Ser. No. 09/478,819, filed Jan. 5, 2000, now U.S. Pat. No. 6,488,892; Ser. No. 09/629,599, filed Jul. 31, 2000, now U.S. Pat. No. 6,469,311; Ser. No. 09/710,061, filed Nov. 10, 2000 now U.S. Pat. No. 6,825,921; Ser. No. 09/733,370, filed Dec. 8, 2000, now abandoned; Ser. No. 09/759,711, filed Jan. 12, 2001 now abandoned; Ser. No. 09/765,869, filed Jan. 19, 2001, now U.S. Pat. No. 6,466,316; Ser. No. 09/767,434, filed Jan. 22, 2001, now U.S. Pat. No. 6,486,947; Ser. No. 09/778,224, filed Feb. 6, 2001 now U.S. Pat. No. 6,838,051; Ser. No. 09/836,575, filed Apr. 16, 2001, now abandoned; Ser. No. 10/004,647, filed Dec. 3, 2001 now U.S. Pat. No. 6,498,335; Ser. No. 10/012,255, filed Nov. 12, 2001 now abandoned; and Ser. No. 10/041,532, filed Jan. 7, 2002, now abandoned.

U.S. patent application Ser. No. 09/144,578, in turn, claims priority from various U.S., PCT, and provisional patent applications. The '578 application is a continuation of the following patent applications: U.S. patent application Ser. No. 09/062,472, filed Apr. 17, 1998, now U.S. Pat. No. 6,071,748; PCT Patent Application Ser. No. PCT/US98/14575, filed Jul. 15, 1998, now abandoned; U.S. patent application Ser. No. 09/118,141, filed Jul. 16, 1998, now U.S. Pat. No. 6,313,960; U.S. patent application Ser. No. 09/118,310, filed Jul. 16, 1998, now U.S. Pat. No. 6,033,100; and U.S. patent application Ser. No. 09/118,341, filed Jul. 16, 1998, now U.S. Pat. No. 6,025,985. These parent applications, in turn, claim priority from additional applications, as identified therein. The '578 application also (directly and/or through its parent applications) is based upon and claims benefit under 35 U.S.C. § 119(e) of the following U.S. provisional patent applications, each of which is now expired: Ser. No. 60/052,876, filed Jul. 16, 1997; Ser. No. 60/059,639, filed Sep. 20, 1997; Ser. No. 60/063,811, filed Oct. 31, 1997; Ser. No. 60/072,499, filed Jan. 26, 1998; Ser. No. 60/072,780, filed Jan. 27, 1998; Ser. No. 60/075,414, filed Feb. 20, 1998; Ser. No. 60/075,806, filed Feb. 24, 1998; Ser. No. 60/082,253, filed Apr. 17, 1998; Ser. No. 60/084,167, filed May 4, 1998; Ser. No. 60/085,335, filed May 13, 1998; Ser. No. 60/085,500, filed May 14, 1998; Ser. No. 60/089,848, filed Jun. 19, 1998; Ser. No. 60/094,275, filed Jul. 27, 1998; Ser. No. 60/094,276, filed Jul. 27, 1998; and Ser. No. 60/094,306, filed Jul. 27, 1998.

U.S. patent application Ser. No. 09/302,158, in turn, is a divisional continuation application of U.S. patent application Ser. No. 09/146,081, filed Sep. 2, 1998, now U.S. Pat. No. 6,187,267. The '081 application, in turn, is a continuation of the following patent applications: U.S. patent application Ser. No. 09/062,472, filed Apr. 17, 1998, now U.S. Pat. No. 6,071,748; PCT Patent Application Ser. No. PCT/US98/14575, filed Jul. 15, 1998, now abandoned; U.S. patent application Ser. No. 09/118,141, filed Jul. 16, 1998, now U.S. Pat. No. 6,313,960; U.S. patent application Ser. No. 09/118,310, filed Jul. 16, 1998, now U.S. Pat. No. 6,033,100; U.S. patent application Ser. No. 09/118,341, filed Jul. 16, 1998, now U.S. Pat. No. 6,025,985; U.S. patent application Ser. No. 09/144,575, filed Aug. 31, 1998, now U.S. Pat. No. 6,159,425; and U.S. patent application Ser. No. 09/144,578, filed Aug. 31, 1998 now U.S. Pat. No. 6,499,366. These parent applications, in turn, claim priority from additional applications, as identified therein. The '081 application, in turn, also (directly and/or through its parent applications) is based upon and claims benefit under 35 U.S.C. § 119(e) of the following U.S. provisional patent applications, each of which is now expired: Ser. No. 60/052,876, filed Jul. 16, 1997; Ser. No. 60/059,639, filed Sep. 20, 1997; Ser. No. 60/063,811, filed Oct. 31, 1997; Ser. No. 60/072,499, filed Jan. 26, 1998; Ser. No. 60/072,780, filed Jan. 27, 1998; Ser. No. 60/075,414, filed Feb. 20, 1998; Ser. No. 60/075,806, filed Feb. 24, 1998; Ser. No. 60/082,253, filed Apr. 17, 1998; Ser. No. 60/084,167, filed May 4, 1998; Ser. No. 60/085,335, filed May 13, 1998; Ser. No. 60/085,500, filed May 14, 1998; Ser. No. 60/089,848, filed Jun. 19, 1998; Ser. No. 60/094,275, filed Jul. 27, 1998; Ser. No. 60/094,276, filed Jul. 27, 1998; and Ser. No. 60/094,306, filed Jul. 27, 1998.

U.S. patent application Ser. No. 09/349,733, in turn, claims priority from various U.S., PCT, and provisional patent applications. The '733 application is a continuation of the following patent applications: U.S. patent application Ser. No. 09/062,472, filed Apr. 17, 1998, now U.S. Pat. No. 6,071,748; U.S. patent application Ser. No. 09/156,318, filed Sep. 18, 1998, now U.S. Pat. No. 6,258,326; U.S. patent application Ser. No. 09/160,533, filed Sep. 24, 1998, now U.S. Pat. No. 6,097,025; PCT Patent Application Ser. No. PCT/US98/23095, filed Oct. 30, 1998, now abandoned; PCT Patent Application Ser. No. PCT/US99/01656, filed Jan. 25, 1999, now abandoned; PCT Patent Application Ser. No. PCT/US99/03678, filed Feb. 19, 1999, now abandoned; and PCT Patent Application Ser. No. PCT/US99/08410, filed Apr. 16, 1999, now abandoned. These parent applications, in turn, claim priority from additional applications, as identified therein. The '733 application, in turn, also (directly and/or through its parent applications) is based upon and claims benefit under 35 U.S.C. § 119(e) of the following U.S. provisional patent applications, each of which is now expired: Ser. No. 60/092,203, filed Jul. 9, 1998; Ser. No. 60/094,275, filed Jul. 27, 1998; Ser. No. 60/094,276, filed Jul. 27, 1998; Ser. No. 60/094,306, filed Jul. 27, 1998; Ser. No. 60/100,817, filed Sep. 18, 1998; Ser. No. 60/100,951, filed Sep. 18, 1998; Ser. No. 60/104,964, filed Oct. 20, 1998; Ser. No. 60/114,209, filed Dec. 29, 1998; Ser. No. 60/116,113, filed Jan. 15, 1999; Ser. No. 60/117,278, filed Jan. 26, 1999; Ser. No. 60/119,884, filed Feb. 12, 1999; Ser. No. 60/121,229, filed Feb. 23, 1999; Ser. No. 60/124,686, filed Mar. 16, 1999; Ser. No. 60/125,346, filed Mar. 19, 1999; Ser. No. 60/126,661, filed Mar. 29, 1999; Ser. No. 60/130,149, filed Apr. 20, 1999; Ser. No. 60/132,262, filed May 3, 1999; Ser. No. 60/132,263, filed May 3, 1999; Ser. No. 60/135,284, filed May 21, 1999; Ser. No. 60/136,566, filed May 28, 1999; Ser. No. 60/138,311, filed Jun. 9, 1999; Ser. No. 60/138,438, filed Jun. 10, 1999; Ser. No. 60/138,737, filed Jun. 11, 1999; Ser. No. 60/138,893, filed Jun. 11, 1999; and Ser. No. 60/142,721, filed Jul. 7, 1999.

U.S. patent application Ser. No. 09/478,819, in turn, is a continuation of PCT Patent Application Ser. No. PCT/US99/08410, filed Apr. 16, 1999, now abandoned. The '08410 application, in turn, is a continuation of the following U.S. patent applications: Ser. No. 09/062,472, filed Apr. 17, 1998, now U.S. Pat. No. 6,071,748; Ser. No. 09/156,318, filed Sep. 18, 1998, now U.S. Pat. No. 6,258,326; and Ser. No. 09/160,533, filed Sep. 24, 1998, now U.S. Pat. No. 6,097,025. These parent applications, in turn, claim priority from additional applications, as identified therein. The '08410 application, in turn, also (directly and/or through its parent applications) is based upon and claims benefit under 35 U.S.C. § 119(e) of the following U.S. provisional patent applications, each of which is now expired: Ser. No. 60/085,500, filed May 14, 1998; Ser. No. 60/089,848, filed Jun. 19, 1998; Ser. No. 60/114,209, filed Dec. 29, 1998; and Ser. No. 60/119,829, filed Feb. 12, 1999.

U.S. patent application Ser. No. 09/629,599, in turn, is a continuation of U.S. patent application Ser. No. 09/160,533, filed Sep. 24, 1998, now U.S. Pat. No. 6,097,025. The '533 application, in turn, is a continuation of the following patent applications: U.S. patent application Ser. No. 09/062,472, filed Apr. 17, 1998, now U.S. Pat. No. 6,071,748; PCT Patent Application Ser. No. PCT/US98/14575, filed Jul. 15, 1998, now abandoned; U.S. patent application Ser. No. 09/118,141, filed Jul. 16, 1998, now U.S. Pat. No. 6,313,960; U.S. patent application Ser. No. 09/118,310, filed Jul. 16, 1998, now U.S. Pat. No. 6,033,100; U.S. patent application Ser. No. 09/118,341, filed Jul. 16, 1998, now U.S. Pat. No. 6,025,985; U.S. patent application Ser. No. 09/144,575, filed Aug. 31, 1998, now U.S. Pat. No. 6,159,425; U.S. patent application Ser. No. 09/144,578, filed Aug. 31, 1998; U.S. patent application Ser. No. 09/146,081, filed Sep. 2, 1998, now U.S. Pat. No. 6,187,267; U.S. patent application Ser. No. 09/156,318, filed Sep. 18, 1998, now U.S. Pat. No. 6,258,326; and U.S. patent application Ser. No. 09/478,819, filed Jan. 5, 2000, now U.S. Pat. No. 6,488,892. These parent applications, in turn, claim priority from additional applications, as identified therein. The '533 application, in turn, also (directly and/or through its parent applications) is based upon and claims benefit under 35 U.S.C. § 119(e) of the following U.S. provisional patent applications, each of which is now expired: Ser. No. 60/063,811, filed Oct. 31, 1997; Ser. No. 60/072,499, filed Jan. 26, 1998; Ser. No. 60/072,780, filed Jan. 27, 1998; Ser. No. 60/075,414, filed Feb. 20, 1998; Ser. No. 60/075,806, filed Feb. 24, 1998; Ser. No. 60/082,253, filed Apr. 17, 1998; Ser. No. 60/084,167, filed May 4, 1998; Ser. No. 60/085,335, filed May 13, 1998; Ser. No. 60/085,500, filed May 14, 1998; Ser. No. 60/089,848, filed Jun. 19, 1998; Ser. No. 60/094,275, filed Jul. 27, 1998; Ser. No. 60/094,276, filed Jul. 27, 1998; Ser. No. 60/094,306, filed Jul. 27, 1998; Ser. No. 60/100,817, filed Sep. 18, 1998; and Ser. No. 60/100,951, filed Sep. 18, 1998.

U.S. patent application Ser. No. 09/710,061, in turn, is based upon and claims benefit under 35 U.S.C. § 119(e) of U.S. Provisional Patent Application Ser. No. 60/164,633, filed Nov. 10, 1999, now expired.

U.S. patent application Ser. No. 09/733,370, in turn, is a continuation of U.S. patent application Ser. No. 09/144,575, filed Aug. 31, 1998, now U.S. Pat. No. 6,159,425. The '575 application, in turn, is a continuation of the following patent applications: U.S. patent application Ser. No. 09/062,472, filed Apr. 17, 1998, now U.S. Pat. No. 6,071,748; PCT Patent Application Ser. No. PCT/US98/14575, filed Jul. 15, 1998, now abandoned; U.S. patent application Ser. No. 09/118,141, filed Jul. 16, 1998, now U.S. Pat. No. 6,313,960; U.S. patent application Ser. No. 09/118,310, filed Jul. 16, 1998, now U.S. Pat. No. 6,033,100; and U.S. patent application Ser. No. 09/118,341, filed Jul. 16, 1998, now U.S. Pat. No. 6,025,985. These parent applications, in turn, claim priority from additional applications, as identified therein. The '575 application, in turn, also (directly and/or through its parent applications) is based upon and claims benefit under 35 U.S.C. § 119(e) of the following U.S. Provisional Patent Applications, each of which is now expired: Ser. No. 60/052,876, filed Jul. 16, 1997; Ser. No. 60/059,639, filed Sep. 20, 1997; Ser. No. 60/063,811, filed Oct. 31, 1997; Ser. No. 60/072,499, filed Jan. 26, 1998; Ser. No. 60/072,780, filed Jan. 27, 1998; Ser. No. 60/075,414, filed Feb. 20, 1998; Ser. No. 60/075,806, filed Feb. 24, 1998; Ser. No. 60/082,253, filed Apr. 17, 1998; Ser. No. 60/084,167, filed May 4, 1998; Ser. No. 60/085,335, filed May 13, 1998; Ser. No. 60/085,500, filed May 14, 1998; Ser. No. 60/089,848, filed Jun. 19, 1998; Ser. No. 60/094,275, filed Jul. 27, 1998; Ser. No. 60/094,276, filed Jul. 27, 1998; and Ser. No. 60/094,306, filed Jul. 27, 1998.

U.S. patent application Ser. No. 09/759,711, in turn, is a continuation of PCT Patent Application Ser. No. PCT/US99/16057, filed Jul. 15, 1999, now abandoned. The '16057 application, in turn, is a continuation of the following applications: U.S. patent application Ser. No. 09/160,533, filed Sep. 24, 1998, now U.S. Pat. No. 6,097,025; and PCT Patent Application Ser. No. PCT/US98/14575, filed Jul. 15, 1998, now abandoned. These parent applications, in turn, claim priority from additional applications, as identified therein. The '16057 application, in turn, also is based upon and claims benefit under 35 U.S.C. § 119(e) directly from U.S. Provisional Patent Application Ser. No. 60/093,838, filed Jul. 22, 1998, now expired.

U.S. patent application Ser. No. 09/765,869, in turn, is a continuation of PCT Patent Application Ser. No. PCT/US99/16621, filed Jul. 23, 1999, now abandoned, which, in turn, is based upon and claims benefit under 35 U.S.C. § 119(e) of the following U.S. provisional patent applications, each of which is now expired: Ser. No. 60/094,275, filed Jul. 27, 1998; Ser. No. 60/117,278, filed Jan. 26, 1999; and Ser. No. 60/136,566, filed May 28, 1999.

U.S. patent application Ser. No. 09/767,434, in turn, is a continuation of PCT Patent Application Ser. No. PCT/US99/16453, filed Jul. 21, 1999, which, in turn, is based upon and claims benefit under 35 U.S.C. § 119(e) of the following U.S. provisional patent applications, each of which is now expired: Ser. No. 60/093,768, filed Jul. 22, 1998; and Ser. No. 60/143,185, filed Jul. 9, 1999.

U.S. patent application Ser. No. 09/778,224, in turn, is a continuation of U.S. patent application Ser. No. 09/777,343, filed Feb. 5, 2001 now U.S. Pat. No. 6,902,703, which, in turn, is a continuation of PCT Patent Application Ser. No. PCT/US00/12277, filed May 3, 2000, now abandoned, which, in turn, is based upon and claims benefit under 35 U.S.C. § 119(e) of the following U.S. provisional patent applications, each of which is now expired: Ser. No. 60/132,262, filed May 3, 1999; Ser. No. 60/132,263, filed May 3, 1999; Ser. No. 60/138,737, filed Jun. 11, 1999; Ser. No. 60/138,893, filed Jun. 11, 1999; Ser. No. 60/153,251, filed Sep. 10, 1999; and Ser. No. 60/167,301, filed Nov. 24, 1999.

U.S. patent application Ser. No. 09/836,575, in turn, is based upon and claims benefit under 35 U.S.C. § 119(e) of U.S. Provisional Patent Application Ser. No. 60/190,265, filed Mar. 17, 2000, now expired.

U.S. patent application Ser. No. 10/004,647, in turn, is a continuation of U.S. patent application Ser. No. 09/643,221, filed Aug. 18, 2000, now U.S. Pat. No. 6,326,605, which, in turn, is a continuation of PCT Patent Application Ser. No. PCT/US99/03678, filed Feb. 19, 1999. The '03678 application, in turn, is a continuation of the following patent applications: U.S. patent application Ser. No. 09/062,472, filed Apr. 17, 1998, now U.S. Pat. No. 6,071,748; U.S. patent application Ser. No. 09/160,533, filed Sep. 24, 1998, now U.S. Pat. No. 6,097,025; PCT Patent Application Ser. No. PCT/US98/23095, filed Oct. 30, 1998, now abandoned; and PCT Application Ser. No. PCT/US99/01656, filed Jan. 25, 1999, now abandoned. These parent applications, in turn, claim priority from additional applications, as identified therein. The '03678 application, in turn, also (directly and/or through its parent applications) is based upon and claims benefit under 35 U.S.C. § 119(e) of the following U.S. provisional patent applications, each of which is now expired: Ser. No. 60/075,414, filed Feb. 20, 1998; Ser. No. 60/082,253, filed Apr. 17, 1998; and Ser. No. 60/100,951, filed Sep. 18, 1998.

U.S. patent application Ser. No. 10/012,255, in turn, is a continuation-in-part of the following U.S. patent applications: Ser. No. 09/626,208, filed Jul. 26, 2000, now abandoned; Ser. No. 09/766,131, filed Jan. 19, 2001, now abandoned; Ser. No. 09/765,874, filed Jan. 19, 2001, now U.S. Pat. No. 6,483,582; Ser. No. 09/767,316, filed Jan. 22, 2001 now U.S. Pat. No. 6,503,719; Ser. No. 09/767,579, filed Jan. 22, 2001, now U.S. Pat. No. 6,317,207; Ser. No. 09/770,720, filed Jan. 25, 2001, now abandoned; and Ser. No. 09/722,247, filed Nov. 24, 2000, now abandoned. U.S. patent application Ser. No. 09/626,208, in turn, is a continuation of PCT Patent Application Ser. No. PCT/US99/01656, filed Jan. 25, 1999, now abandoned. The '01656 application is a continuation-in-part of the following patent applications: U.S. patent application Ser. No. 09/062,472, filed Apr. 17, 1998, now U.S. Pat. No. 6,071,748; U.S. patent application Ser. No. 09/160,533, filed Sep. 24, 1998, now U.S. Pat. No. 6,097,025; and PCT Application Ser. No. PCT/US98/23095, filed Oct. 30, 1998, now abandoned. These parent applications, in turn, claim priority from additional applications, as identified therein. The '01656 application also is based upon and claims benefit under 35 U.S.C. § 119(e) directly from the following U.S. provisional patent applications, each of which is now expired: Ser. No. 60/072,499, filed Jan. 26, 1998; Ser. No. 60/072,780, filed Jan. 27, 1998; Ser. No. 60/075,806, filed Feb. 24, 1998; and Ser. No. 60/084,167, filed May 4, 1998. U.S. patent application Ser. No. 09/766, 131, in turn, is a continuation of PCT Patent Application Ser. No. PCT/US99/16286, filed Jul. 26, 1999, now abandoned, which is based upon and claims benefit under 35 U.S.C. § 119(e) of U.S. Provisional Patent Application Ser. No. 60/094,306, filed Jul. 27, 1998, now expired. U.S. patent application Ser. No. 09/765,874, in turn, is a continuation of PCT Patent Application Ser. No. PCT/US99/16287, filed Jul. 26, 1999, now abandoned, which is based upon and claims benefit under 35 U.S.C. § 119(e) of U.S. Provisional Patent Application Ser. No. 60/094,276, filed Jul. 27, 1998, now expired. U.S. patent application Ser. No. 09/767,316, in turn, is a continuation of PCT Patent Application Ser. No. PCT/US00/00895, filed Jan. 14, 2000, now abandoned, which is based upon and claims benefit under 35 U.S.C. § 119(e) of the following U.S. provisional patent applications, each of which is now expired: Ser. No. 60/116,113, filed Jan. 15, 1999; Ser. No. 60/135,284, filed May 21, 1999; and Ser. No. 60/167,463, filed Nov. 24, 1999. U.S. patent application Ser. No. 09/767,579, in turn, is a continuation of PCT Patent Application Ser. No. PCT/US00/04543, filed Feb. 22, 2000, now abandoned, which is based upon and claims benefit under 35 U.S.C. § 119(e) of U.S. Provisional Patent Application Ser. No. 60/121,229, filed Feb. 23, 1999, now expired. U.S. patent application Ser. No. 09/770,720, in turn, is a continuation of PCT Patent Application Ser. No. PCT/US00/06841, filed Mar. 15, 2000. The '06841 application is a continuation-in-part of the following patent applications: PCT Patent Application Ser. No. PCT/US99/08410, filed Apr. 16, 1999, now abandoned; U.S. patent application Ser. No. 09/349,733, filed Jul. 8, 1999, now abandoned; PCT Patent Application Ser. No. PCT/US00/00895, filed Jan. 14, 2000, now abandoned; and U.S. patent application Ser. No. 09/494,407, filed Jan. 28, 2000, now U.S. Pat. No. 6,297, 108. These parent applications, in turn, claim priority from additional applications, as identified therein. The '06841 application also is based upon and claims benefit under 35 U.S.C. § 119(e) directly from the following U.S. provisional patent applications, each of which is now expired: Ser. No. 60/124,686, filed Mar. 16, 1999; Ser. No. 60/125,346, filed Mar. 19, 1999; Ser. No. 60/135,284, filed May 21, 1999; Ser. No. 60/184,719, filed Feb. 24, 2000; and Ser. No. 60/184, 924, filed Feb. 25, 2000. U.S. patent application Ser. No. 09/722,247, in turn, is a continuation-in-part of U.S. patent application Ser. No. 09/626,208, filed Jul. 26, 2000, now abandoned, which claims priority from additional applications, as indicated above. U.S. patent application Ser. No. 09/722,247 also is based upon and claims benefit under 35 U.S.C. § 119(e) directly from the following U.S. provisional patent applications, each of which is now expired: Ser. No. 60/167,463, filed Nov. 24, 1999; and Ser. No. 60/182,419, filed Feb. 14, 2000.

U.S. patent application Ser. No. 10/041,532, in turn, is a continuation of PCT Patent Application Ser. No. PCT/US00/ 18547, filed Jul. 7, 2000, now abandoned, which, in turn, is based upon and claims benefit under 35 U.S.C. § 119(e) of U.S. Provisional Patent Application Ser. No. 60/142,721, filed Jul. 7, 1999, now expired.

The above-identified U.S., PCT, and provisional priority patent applications are each incorporated herein by reference in their entirety for all purposes.

CROSS-REFERENCES TO ADDITIONAL MATERIALS

This application also incorporates by reference in their entirety for all purposes the following additional materials: K. E. van Holde, PHYSICAL BIOCHEMISTRY ($2^{nd}$ ed. 1985); William Bains, BIOTECHNOLOGY FROM A TO Z (1993); Richard P. Haugland, HANDBOOK OF FLUORESCENT PROBES AND RESEARCH CHEMICALS ($6^{th}$ ed. 1996); Paul Horowitz & Winfield Hill, THE ART OF ELECTRONICS (1980); Joseph R. Lakowicz, PRINCIPLES OF FLUORESCENCE SPECTROSCOPY ($2^{nd}$ ed. 1999); Bob Sinclair, EVERYTHING'S GREAT WHEN IT SITS ON A CHIP: A BRIGHT FUTURE FOR DNA ARRAYS, 13 THE SCIENTIST, May 24, 1999, at 18; and Charles R. Cantor and Paul R. Schimmel, BIOPHYSICAL CHEMISTRY (1980).

FIELD OF THE INVENTION

The invention relates to light detection, and more particularly to efficient, broad-range light-detection systems.

BACKGROUND

Systems that involve the detection of light are used in a variety of contexts. For example, systems that involve the detection and analysis of light are used in performing optical spectroscopic assays, including luminescence and absorption assays. These assays may be used to characterize the components and properties of molecular systems, and recently have been used in high-throughput screening procedures to identify candidate drug compounds.

High measurement throughput and high measurement precision are two valuable characteristics of light detection systems, particularly for drug discovery. Throughput and precision largely depend on the architecture and design of the detection system. However, the end-user can fine-tune the throughput and precision on some detection systems by adjusting instrument settings. Of these tunable settings, the most significant is detection time. In detection modes that use continuous light sources and in chemiluminescence modes, the detection time may be determined by setting an "integration" time. In detection modes that use a flash lamp, the detection time may be determined by the number of times the lamp flashes.

Throughput typically is increased by decreasing the detection time. However, many photoluminescence and chemiluminescence assays are shot-noise limited, so that decreasing the detection time results in lower detection precision. In cases such as these, where the time and precision are inversely related (i.e., where longer measurements generally correspond to more precise measurements), the end-user endeavors to strike a balance between detection throughput and detection precision. This balance often is achieved by trial-and-error: the end-user prepares test samples, and then reads the samples repeatedly in the detection system to empirically optimize the trade-off between throughput and precision.

The above process can be time consuming and tedious for the user, even for simple assays in which every sample has a similar photoluminescence or chemiluminescence intensity. However, in many assays, intensities vary from sample to sample. These assays are particularly troublesome to optimize. If the user sets a large detection time, such that adequate precision is achieved for low-intensity samples, then high-intensity samples will be "over-detected," with a decrease in overall throughput. Likewise, if the user sets a small detection time, to achieve adequate precision for high-intensity samples, then low-intensity samples will be detected with poor precision. Ultimately, the end-user must compromise either throughput or precision or both.

Light-detection systems may suffer from additional shortcomings. For example, such systems may be limited in range, so that they accurately detect light only within some relatively narrow range of intensities. Such systems also may require user intervention to alter the detection range, if the range may be altered at all. Such systems also may be limited to either discrete or analog detection, so that either they discretely count individual quanta or photons of light, or they integrate an analog value corresponding to such quanta, but they do not do both. Such systems also may require significant periods of time to make measurements. These shortcomings may be found singly or in combination, and these shortcomings may be particularly significant in the context of high-throughput screening, where it may be necessary to perform tens or hundreds of thousands of measurements per day.

SUMMARY

The invention provides, among others, broad-range light-detection systems, including components and methods of use thereof. These systems may include apparatus and methods for detecting light with increased speed and/or detection efficiency, particularly in applications involving repeated analysis of the same sample and/or successive analysis of different samples, and particularly when the sample or samples have a wide range of light intensities. These systems also may include apparatus and methods for detecting light with increased accuracy over a broad range of intensities. These systems also may include apparatus and methods for automatically scaling detection range to improve detection based on the intensity of the detected light.

BRIEF DESCRIPTION OF THE DRAWINGS

FIG. 5 is a schematic view of photoluminescence optical components from the apparatus of FIG. 3.

FIG. 6 is a schematic view of chemiluminescence optical components from the apparatus of FIG. 3.

DETAILED DESCRIPTION

Figure 1:
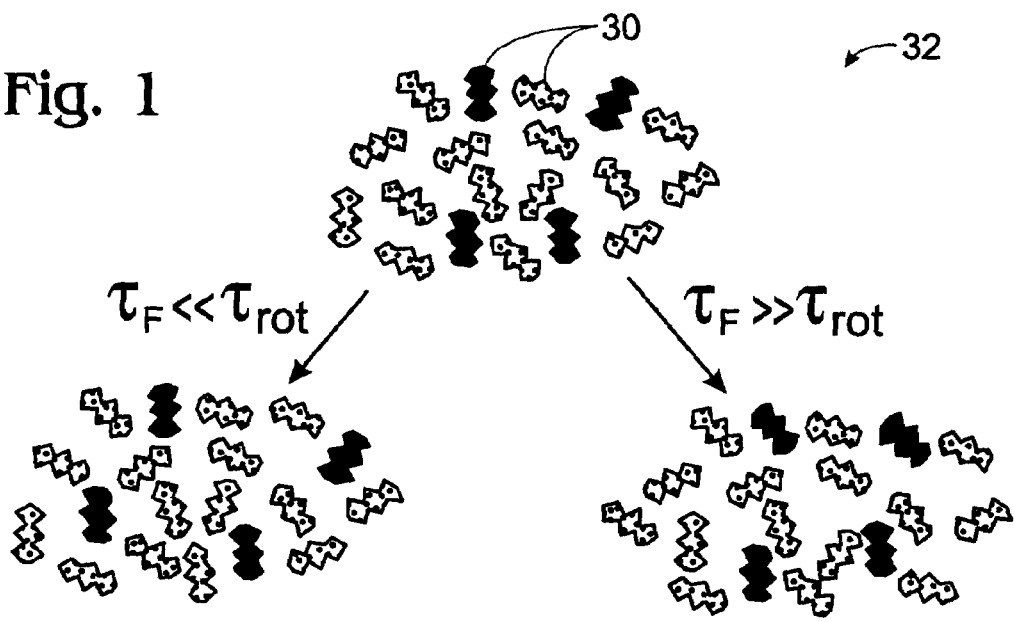
FIG. 1 is a schematic view of fluorescently labeled molecules, showing how molecular reorientation affects fluorescence polarization.

The invention provides, among others, broad-range light-detection systems, including components and methods of use thereof. These systems may include apparatus and methods for detecting light with increased speed and/or detection efficiency, particularly in applications involving repeated analysis of the same sample and/or successive analysis of different samples, and particularly when the sample or samples have a wide range of light intensities. These systems also may include apparatus and methods for detecting light with increased accuracy over a broad range of intensities. These systems also may include apparatus and methods for automatically scaling detection range to improve detection based on the intensity of the detected light. These and other aspects of the invention are described below, including (I) luminescence assays, (II) luminescence apparatus, (III) detection methods, and (IV) examples.

I. Luminescence Assays

Luminescence is the emission of light from excited electronic states of atoms or molecules. Luminescence generally refers to all kinds of light emission, except incandescence, and may include photoluminescence, chemiluminescence, and electrochemiluminescence, among others. In photoluminescence, including fluorescence and phosphorescence, the excited electronic state is created by the absorption of electromagnetic radiation. In chemiluminescence, which includes bioluminescence, the excited electronic state is created by a transfer of chemical energy. In electrochemiluminescence, the excited electronic state is created by an electrochemical process.

Luminescence assays use luminescence emissions from luminescent analytes to study the properties and environment of the analyte, as well as binding reactions and enzymatic activities involving the analyte, among others. In this sense, the analyte may act as a reporter to provide information about another material or target substance that may be the focus of the assay.

Luminescence assays may use various aspects of the luminescence, including its intensity, spectra, polarization, and lifetime, among others. Luminescence assays also may use time-independent (steady-state) and/or time-dependent (time-resolved) properties of the luminescence. Steady-state assays generally are less complicated than time-resolved assays, but generally yield less information.

The remainder of this section describes five exemplary luminescence assays: (A) intensity assays, (B) polarization assays, (C) energy transfer assays, (D) ratio assays, and (E) time-resolved assays. Additional assays, and additional information about the exemplary assays, are described in the patents, patent applications, and other materials cross-referenced above and incorporated herein by reference, including, among others, U.S. patent application Ser. No. 09/349, 733, filed Jul. 8, 1999; U.S. patent application Ser. No. 10/012,255, filed Nov. 12, 2001; and Joseph R. Lakowicz, PRINCIPLES OF FLUORESCENCE SPECTROSCOPY ($2^{nd}$ ed. 1999).

I.A Intensity Assays

Luminescence intensity assays involve monitoring the intensity (or amount per time) of light emitted from a composition. The intensity of emitted light will depend on the extinction coefficient, quantum yield, and number of the luminescent analytes in the composition, among others. These quantities, in turn, will depend on the environment on the analyte, among others, including the proximity and efficacy of quenchers and energy transfer partners. Thus, luminescence intensity assays may be used to study binding reactions, among other applications.

I.B Polarization Assays

Luminescence polarization assays involve the absorption and emission of polarized light, and typically are used to study molecular rotation. (Polarization describes the direction of light's electric field, which generally is perpendicular to the direction of light's propagation.)

FIG. 1 is a schematic view showing how luminescence polarization is affected by molecular rotation. In a luminescence polarization assay, specific molecules 30 within a composition 32 are labeled with one or more luminophores. The composition then is illuminated with polarized excitation light, which preferentially excites luminophores having absorption dipoles aligned parallel to the polarization of the excitation light. These molecules subsequently decay by preferentially emitting light polarized parallel to their emission dipoles. The extent to which the total emitted light is polarized depends on the extent of molecular reorientation during the time interval between luminescence excitation and emission, which is termed the luminescence lifetime, $\tau$. The extent of molecular reorientation in turn depends on the luminescence lifetime and the size, shape, and environment of the reorienting molecule. Thus, luminescence polarization assays may be used to quantify binding reactions and enzymatic activity, among other applications. In particular, molecules rotate via diffusion with a rotational correlation time $\tau_{rot}$ that is proportional to their size. Thus, during their luminescence lifetime, relatively large molecules will not reorient significantly, so that their total luminescence will be relatively polarized. In contrast, during the same time interval, relatively small molecules will reorient significantly, so that their total luminescence will be relatively unpolarized.

The relationship between polarization and intensity is expressed by the following equation:

$$P = \frac{I_\| - I_\perp}{I_\| + I_\perp} \tag{1}$$

Here, P is the polarization, $I_\|$ is the intensity of luminescence polarized parallel to the polarization of the excitation light, and $I_\perp$ is the intensity of luminescence polarized perpendicular to the polarization of the excitation light. If there is little rotation between excitation and emission, $I_\|$ will be relatively large, $I_\perp$ will be relatively small, and P will be close to one. (P may be less than one even if there is no rotation; for example, P may be less than one if the absorption and emission dipoles are not parallel, and P typically will be less than about one-half for mixtures of randomly oriented molecules.) In contrast, if there is significant rotation between absorption and emission, $I_\|$ will be comparable to $I_\perp$ and P will be close to zero. Polarization often is reported in milli-P units (1000×P), which typically will range between 0 and 1000, because P typically will range between zero and one.

Polarization also may be described using other equivalent quantities, such as anisotropy. The relationship between anisotropy and intensity is expressed by the following equation:

$$r = \frac{I_\| - I_\perp}{I_\| + 2I_\perp} \tag{2}$$

Here, r is the anisotropy. Polarization and anisotropy include the same information, although anisotropy may be more simply expressed for systems containing more than one luminophore. In the description and claims that follow, these terms may be used interchangeably, and a generic reference to one should be understood to imply a generic reference to the other.

The relationship between polarization and rotation is expressed by the Perrin equation:

$$\left(\frac{1}{P} - \frac{1}{3}\right) = \left(\frac{1}{P_0} - \frac{1}{3}\right) \cdot \left(1 + \frac{\tau}{\tau_{rot}}\right) \quad (3)$$

Here, $P_0$ is the polarization in the absence of molecular motion (intrinsic polarization), $\tau$ is the luminescence lifetime (inverse decay rate) as described above, and $\tau_{rot}$ is the rotational correlation time (inverse rotational rate) as described above.

The Perrin equation shows that luminescence polarization assays are most sensitive when the luminescence lifetime and the rotational correlation time are similar. Rotational correlation time is proportional to molecular weight, increasing by about 1 nanosecond for each 2,400 dalton increase in molecular weight (for a spherical molecule). For shorter lifetime luminophores, such as fluorescein, which has a luminescence lifetime of roughly 4 nanoseconds, luminescence polarization assays are most sensitive for molecular weights less than about 40,000 daltons. For longer lifetime probes, such as Ru(bpy)$_2$dcbpy (ruthenium 2,2'-dibipyridyl 4,4'-dicarboxyl-2,2'-bipyridine), which has a lifetime of roughly 400 nanoseconds, luminescence polarization assays are most sensitive for molecular weights between about 70,000 daltons and 4,000,000 daltons.

I.C Energy Transfer Assays

Energy transfer is the transfer of luminescence energy from a donor luminophore to an acceptor without emission by the donor. In energy transfer assays, a donor luminophore is excited from a ground state into an excited state by absorption of a photon. If the donor luminophore is sufficiently close to an acceptor, excited-state energy may be transferred from the donor to the acceptor, causing donor luminescence to decrease and acceptor luminescence to increase (if the acceptor is luminescent). The efficiency of this transfer is very sensitive to the separation R between donor and acceptor, decaying as $1/R^6$. Energy transfer assays use energy transfer to monitor the proximity of donor and acceptor, which in turn may be used to monitor a variety of processes, including the presence or activity of an analyte, the presence of or a change in membrane potential, and others.

Energy transfer assays may focus on an increase in energy transfer as donor and acceptor are brought into proximity. These assays may be used to monitor binding, as between two molecules X and Y to form a complex X:Y. Here, colon (:) represents a noncovalent interaction. In these assays, one molecule is labeled with a donor D, and the other molecule is labeled with an acceptor A, such that the interaction between X and Y is not altered appreciably. Independently, D and A may be covalently attached to X and Y, or covalently attached to binding partners of X and Y.

Energy transfer assays also may focus on a decrease in energy transfer as donor and acceptor are separated. These assays may be used to monitor cleavage, as by hydrolytic digestion of doubly labeled substrates (peptides, nucleic acids). In one application, two portions of a polypeptide are labeled with D and A, so that cleavage of the polypeptide by a protease such as an endopeptidase will separate D and A and thereby reduce energy transfer. In another application, two portions of a nucleic acid are labeled with D and A, so that cleavage by a nuclease such as a restriction enzyme will separate D and A and thereby reduce energy transfer.

Energy transfer between D and A may be monitored in various ways. For example, energy transfer may be monitored by observing an energy-transfer induced decrease in the emission intensity of D and increase in the emission intensity of A (if A is a luminophore). Energy transfer also may be monitored by observing an energy-transfer induced decrease in the lifetime of D and increase in the apparent lifetime of A.

In a preferred mode, a long-lifetime luminophore is used as a donor, and a short-lifetime luminophore is used as an acceptor. Suitable long-lifetime luminophores include metal-ligand complexes containing ruthenium, osmium, etc., and lanthanide chelates containing europium, terbium, etc. In time-gated assays, the donor is excited using a flash of light having a wavelength near the excitation maximum of D. Next, there is a brief wait, so that electronic transients and/or short-lifetime background luminescence can decay. Finally, donor and/or acceptor luminescence intensity is detected and integrated. In frequency-domain assays, the donor is excited using time-modulated light, and the phase and/or modulation of the donor and/or acceptor emission is monitored relative to the phase and/or modulation of the excitation light. In both assays, donor luminescence is reduced if there is energy transfer, and acceptor luminescence is observed only if there is energy transfer.

I.D Ratio Assays

Ratio assays involve the measurement and comparison of two or more different optical signals. Typically, one of the signals represents a data or reporter signal, providing information on a parameter of interest, and another of the signals represents a control signal, providing calibrating information (such as location and/or concentration) for use with the first signal. For example, the first signal might report on pH, ionic (e.g., calcium) concentration, electrical potential, and/or the like, while the second signal might report on the concentration of the reporter giving rise to the first signal.

The optical signals generally may be generated using any suitable detectable optical phenomenon, including absorption, transmission, emission, reflection, and/or the like. However, generally the optical signals arise from emission, such as photoluminescence emission. In some cases, emission optical signals arise from two different luminophores, coupled to a common carrier or present in the same sample. In other cases, emission optical signals arise from the same luminophore, sampled, for example, at different wavelengths and/or lifetimes. In each case, one (reporter) signal is sensitive to a parameter of interest, while the other (control) signal is at least relatively insensitive to the parameter.

The comparison of the two or more optical signals in a ratio assay may be performed in any suitable manner; however, such comparison typically involves construction of a ratio related to a property of the light, such as amount, intensity, and so on.

I.E Time-Resolved Assays

Time-resolved assays involve measuring the time course of luminescence emission. Time-resolved assays may be conducted in the time domain or in the frequency domain. In a time-domain measurement, the time course of luminescence is monitored directly. Typically, a composition containing a luminescent analyte is illuminated using a narrow pulse of light, and the time dependence of the intensity of the resulting luminescence emission is observed, although other protocols also may be used. For a simple molecule, the luminescence commonly follows a single-exponential decay.

In a frequency-domain measurement, the time course of luminescence is monitored indirectly, in frequency space. Typically, the composition is illuminated using light whose intensity is modulated sinusoidally at a single modulation frequency f, although other protocols (such as transforming time-domain data into the frequency domain) also may be used. The intensity of the resulting luminescence emission is modulated at the same frequency as the excitation light. However, the emission will lag the excitation by a phase angle (phase) $\phi$, and the intensity of the emission will be demodulated relative to the intensity of the excitation by a demodulation factor (modulation) M.

Figure 2:
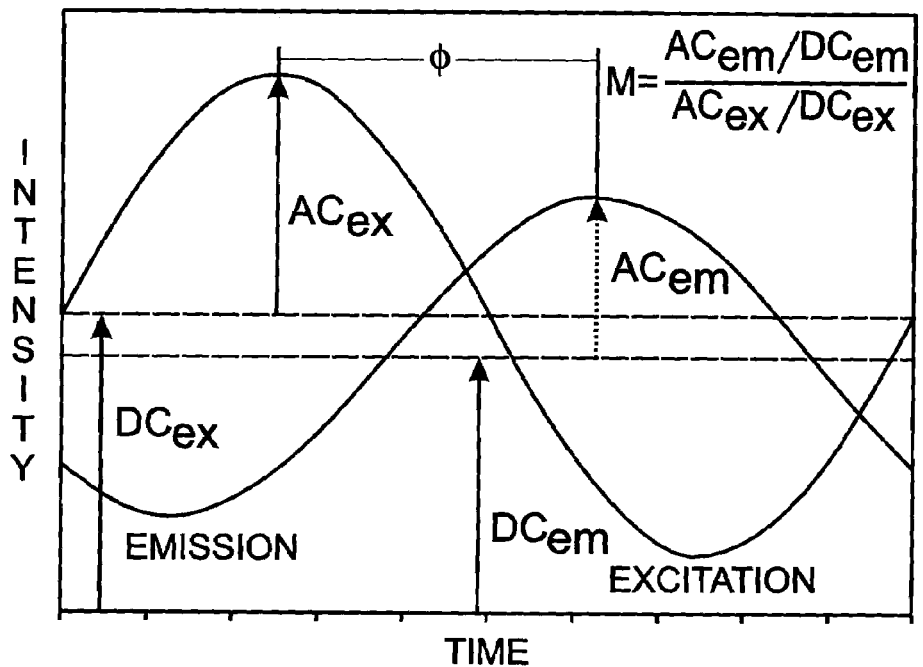
FIG. 2 is a schematic view of a frequency-domain time-resolved measurement, showing the definitions of phase angle (phase) $\phi$ and demodulation factor (modulation) M.

FIG. 2 shows the relationship between emission and excitation in a single-frequency frequency-domain experiment. The phase $\phi$ is the phase difference between the excitation and emission. The modulation M is the ratio of the AC amplitude to the DC amplitude for the emission, relative to the ratio of the AC amplitude to the DC amplitude for the excitation. The phase and modulation are related to the luminescence lifetime $\tau$ by Equations 4 and 5.

$$\omega\tau = \tan(\phi) \quad (4)$$

$$\omega\tau = \sqrt{\frac{1}{M^2} - 1} \quad (5)$$

Here $\omega$ is the angular modulation frequency, which equals $2\pi$ times the modulation frequency. For maximum sensitivity, the angular modulation frequency should be roughly the inverse of the luminescence lifetime. Lifetimes of interest in high-throughput screening vary from less than 1 nanosecond to greater than 10 microseconds. Therefore, instruments for high-throughput screening should be able to cover modulation frequencies from 20 kHz to 200 MHz.

II. Luminescence Apparatus

FIGS. 3–6 show an exemplary apparatus 90 for detecting light emitted by an analyte in a composition. Apparatus 90 may include (1) a stage for supporting the composition, (2) one or more light sources for delivering light to a composition, (3) one or more detectors for receiving light transmitted from the composition and converting it to a signal, (4) first and second optical relay structures for relaying light between the light source, composition, and detector, and/or (5) a processor for analyzing the signal from the detector. In many cases, only a subset of these components is used for a particular assay or other application.

Apparatus 90 may be used for a variety of assays, including but not limited to the assays described above. Components of the optical system may be chosen to improve sensitivity and dynamic range for each assay supported by the analyzer. Toward this end, optical components with low intrinsic luminescence may be chosen. In addition, some components may be shared by different modes, whereas other components may be unique to a particular mode. For example, photoluminescence intensity and steady-state photoluminescence polarization modes may share a light source; time-resolved luminescence modes may use their own light source; and chemiluminescence modes may not use a light source. Similarly, photoluminescence and chemiluminescence modes may use different detectors. In some embodiments, the optics may be adapted to improve precision in absorbance measurements, such that the measurements are at least relatively insensitive to meniscus effects (lensing and displacement), for example, as described in U.S. Provisional Patent Application Ser. No. 60/383,198, filed May 22, 2002, which is incorporated herein by reference in its entirety for all purposes.

These and other aspects of exemplary apparatus are described in detail below, including (A) photoluminescence optical system, (B) chemiluminescence optical system, (C) housing, (D) alternative apparatus, and (E) methods. Additional disclosure is included in the patents, patent applications, and other materials cross-referenced above and incorporated herein by reference, including, among others, U.S. Pat. No. 5,355,215, issued Oct. 11, 1994; U.S. Pat. No. 6,097,025, issued Aug. 1, 2000; U.S. Pat. No. 6,232,608, issued May 15, 2001; U.S. Pat. No. 6,236,456, issued May 22, 2001; U.S. patent application Ser. No. 09/777,343, filed Feb. 5, 2001; U.S. patent application Ser. No. 10/061,416, filed Feb. 1, 2002; U.S. patent application Ser. No. 10/003,030, filed Oct. 29, 2001; U.S. patent application Ser. No. 10/012,255, filed Nov. 12, 2001; U.S. patent application Ser. No. 10/218,897, filed Aug. 13, 2002; U.S. Provisional Patent Application Ser. No. 60/383,198, filed May 22, 2002; U.S. Provisional Patent Application Ser. No. 60/383,311, filed May 22, 2002; and Joseph R. Lakowicz, PRINCIPLES OF FLUORESCENCE SPECTROSCOPY ($2^{nd}$ ed. 1999).

II.A Photoluminescence Optical System

As configured here, apparatus 90 includes a continuous light source 100 and a time-modulated light source 102. Apparatus 90 includes light source slots 103a–d for four light sources, although other numbers of light source slots and light sources also could be provided. Light source slots 103a–d function as housings that may surround at least a portion of each light source, providing some protection from radiation and explosion. The direction of light transmission through the photoluminescence optical system is indicated by arrows.

Continuous source 100 provides light for photoluminescence intensity and steady-state photoluminescence polarization assays. Continuous light source 100 may include arc lamps, lasers, laser diodes, and light-emitting diodes (LEDs), among others. A preferred continuous source is a high-intensity, high color temperature xenon arc lamp, such as a Model LX175F CERMAX xenon lamp from ILC Technology, Inc. Color temperature is the absolute temperature in Kelvin at which a blackbody radiator must be operated to have a chromaticity equal to that of the light source. A high color temperature lamp produces more light than a low color temperature lamp, and it may have a maximum output shifted toward or into visible wavelengths and ultraviolet wavelengths where many luminophores absorb. The preferred continuous source has a color temperature of 5600 Kelvin, greatly exceeding the color temperature of about 3000 Kelvin for a tungsten filament source. The preferred source provides more light per unit time than flash sources, increasing sensitivity and reducing read times. Apparatus 90 may include a modulator mechanism configured to vary the intensity of light incident on the composition without varying the intensity of light produced by the light source.

Time-modulated source 102 provides light for time-resolved photoluminescence assays, such as photoluminescence lifetime and time-resolved photoluminescence polarization assays. A preferred time-modulated source is a xenon flash lamp, such as a Model FX-1160 xenon flash lamp from EG&G Electro-Optics. The preferred source produces a "flash" of light for a brief interval before signal detection and is especially well suited for time-domain measurements. Other time-modulated sources include pulsed lasers and LEDs, as well as continuous lamps whose intensity can be modulated extrinsically using a Pockels cell, Kerr cell, or other mechanism. The latter sources are especially well suited for frequency-domain measurements.

The system may include a continuous source 100 and a time-modulated source 102, which, in some embodiments, may produce multichromatic, unpolarized, and incoherent light. Continuous source 100 produces substantially continuous illumination, whereas time-modulated source 102 produces time-modulated illumination. Light from these light sources may be delivered to the sample without modification, or it may be filtered to alter its intensity, spectrum, polarization, or other properties.

Light produced by the light sources follows an excitation optical path to an examination site. Such light may pass through one or more "spectral filters," which generally comprise any mechanism for altering the spectrum of light that is delivered to the sample. Spectrum refers to the wavelength composition of light. A spectral filter may be used to convert white or multichromatic light, which includes light of many colors, into red, blue, green, or other substantially monochromatic light, which includes light of one or only a few colors. In apparatus 90, spectrum is altered by an excitation interference filter 104, which selectively transmits light of preselected wavelengths and selectively absorbs light of other wavelengths. For convenience, excitation interference filters 104 may be housed in an excitation filter wheel 106, which allows the spectrum of excitation light to be changed by rotating a preselected filter into the optical path. Spectral filters also may separate light spatially by wavelength. Examples include gratings, monochromators, and prisms.

Spectral filters are not required for monochromatic ("single color") light sources, such as certain lasers, which output light of only a single wavelength. Therefore, excitation filter wheel 106 may be mounted in the optical path of some light source slots 103a,b, but not other light source slots 103c,d.

Light next passes through an excitation optical shuttle (or switch) 108, which positions an excitation fiber optic cable 110a,b in front of the appropriate light source to deliver light to top or bottom optics heads 112a,b, respectively. The optics heads include various optics for delivering light into the sensed volume and for receiving light transmitted from the sensed volume. Light is transmitted through a fiber optic cable much like water is transmitted through a garden hose. Fiber optic cables can be used easily to turn light around corners and to route light around opaque components of the apparatus. Moreover, fiber optic cables give the light a more uniform intensity profile. A preferred fiber optic cable is a fused silicon bundle, which has low autoluminescence. Despite these advantages, light also can be delivered to the optics heads using other mechanisms, such as mirrors.

Light arriving at the optics head may pass through one or more excitation "polarization filters," which generally comprise any mechanism for altering the polarization of light. Excitation polarization filters may be included with the top and/or bottom optics head. In apparatus 90, polarization is altered by excitation polarizers 114, which are included only with top optics head 112a. Excitation polarization filters 114 may include an s-polarizer S that passes only s-polarized light, a p-polarizer P that passes only p-polarized light, and a blank O that passes substantially all light. Excitation polarizers 114 also may include a standard or ferro-electric liquid crystal display (LCD) polarization switching system. Such a system is faster and more economical than a mechanical switcher. Excitation polarizers 114 also may include a continuous mode LCD polarization rotator with synchronous detection to increase the signal-to-noise ratio in polarization assays. Excitation polarizers 114 may be included in light sources, such as certain lasers, that intrinsically produce polarized light.

Light at one or both optics heads also may pass through an excitation "confocal optics element," which generally comprises any mechanism for focusing light into a "sensed volume." In apparatus 90, the confocal optics element includes a set of lenses 117a–c and an excitation aperture 116 placed in an image plane conjugate to the sensed volume, as shown in FIG. 5. Aperture 116 may be implemented directly, as an aperture, or indirectly, as the end of a fiber optic cable. Lenses 117a,b project an image of aperture 116 onto the sample, so that only a preselected or sensed volume of the sample is illuminated.

Light traveling through the optics heads is reflected and transmitted through a beamsplitter 118, which delivers reflected light to a composition 120 and transmitted light to a light monitor 122. Reflected and transmitted light both pass through lens 117b, which is operatively positioned between beamsplitter 118 and composition 120.

Beamsplitter 118 is used to direct excitation light toward the sample and light monitor, and to direct emission light toward the detector. The beamsplitter is changeable, so that it may be optimized for different assay modes or compositions. If a large number or variety of luminescent molecules are to be studied, the beamsplitter must be able to accommodate light of many wavelengths; in this case, a "50:50" beamsplitter that reflects half and transmits half of the incident light independent of wavelength is optimal. Such a beamsplitter can be used with many types of molecules, while still delivering considerable excitation light onto the composition, and while still transmitting considerable emission light to the detector. If one or a few related luminescent molecules are to be studied, the beamsplitter needs only to be able to accommodate light at a limited number of wavelengths; in this case, a "dichroic" or "multichroic" beamsplitter is optimal. Such a beamsplitter can be designed with cutoff wavelengths for the appropriate set of molecules and will reflect most or substantially all of the excitation and background light, while transmitting most or substantially all of the emission light. This is possible because the reflectivity and transmissivity of the beamsplitter can be varied with wavelength.

Light monitor 122 is used to correct for fluctuations in the intensity of light provided by the light sources; such corrections may be performed by reporting amounts of light detected as a ratio over corresponding times of the luminescence intensity measured by the detector to the excitation light intensity measured by the light monitor. The light monitor also can be programmed to alert the user if the light source fails. A preferred light monitor is a silicon photodiode with a quartz window for low autoluminescence.

The composition (or sample) may be held in a sample holder supported by a stage 123. The composition can include compounds, mixtures, surfaces, solutions, emulsions, suspensions, cell cultures, fermentation cultures, cells, tissues, secretions, and/or derivatives and/or extracts thereof. Analysis of the composition may involve measuring the presence, concentration, or physical properties (including interactions) of a photoluminescent analyte in such a composition. The sample holder can include microplates, microarrays, biochips, or any array of samples in a known format. In apparatus 90, the preferred sample holder is a microplate 124, which includes a plurality of microplate wells 126 for holding compositions. Composition may refer to the contents of a single microplate well, or several microplate wells, depending on the assay. In some embodiments, such as a portable analyzer, the stage may be intrinsic to the instrument.

The sensed volume typically has an hourglass shape, with a cone angle of about 25° and a minimum diameter ranging between 0.1 mm and 2.0 mm. For 96-well and 384-well microplates, a preferred minimum diameter is about 1.5 mm. For 1536-well microplates, a preferred minimum diameter is about 1.0 mm. The size and shape of the sample container may be matched to the size and shape of the sensed volume.

Figure 3:
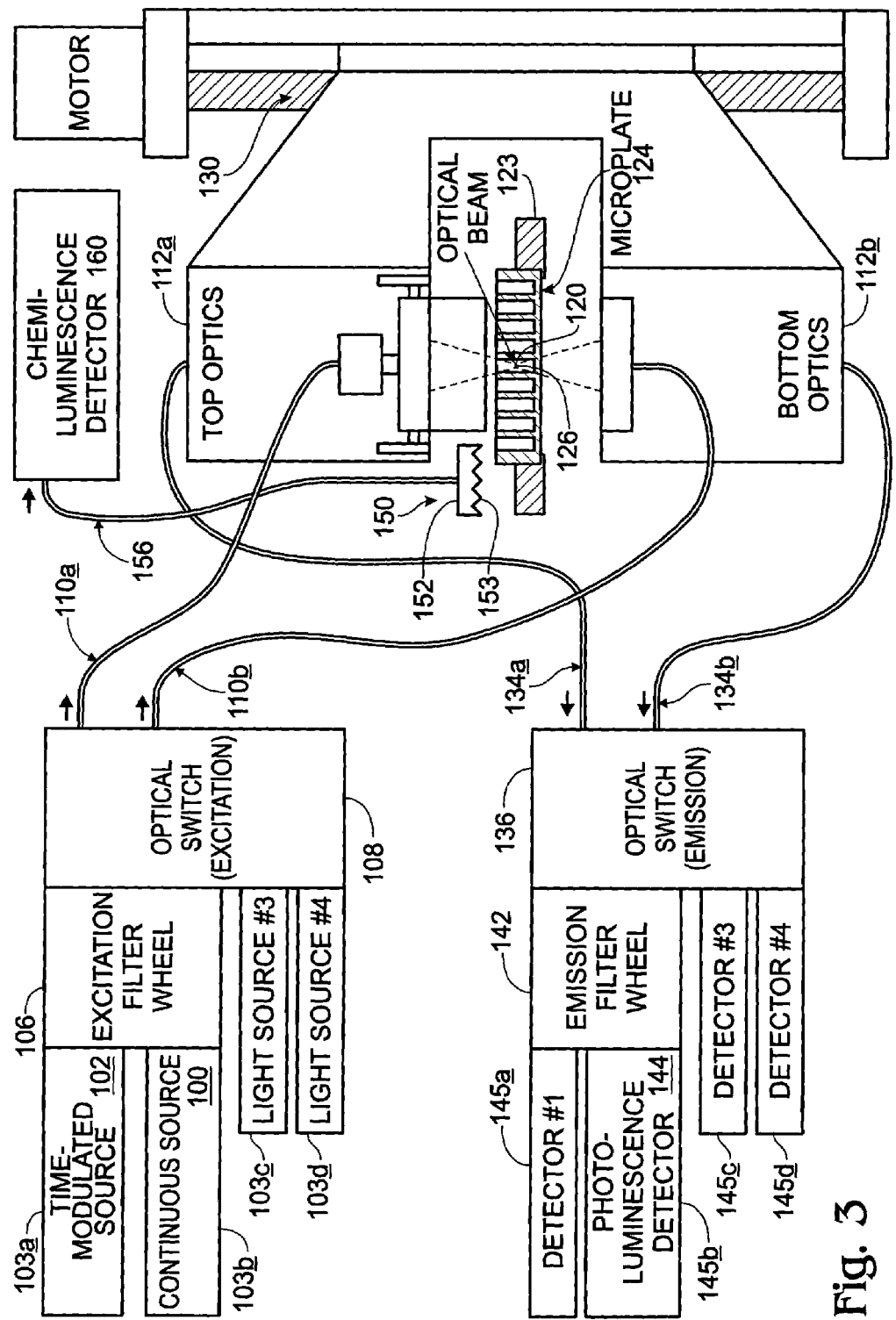
FIG. 3 is a schematic view of an apparatus for detecting light, in accordance with aspects of the invention.
Figure 4:
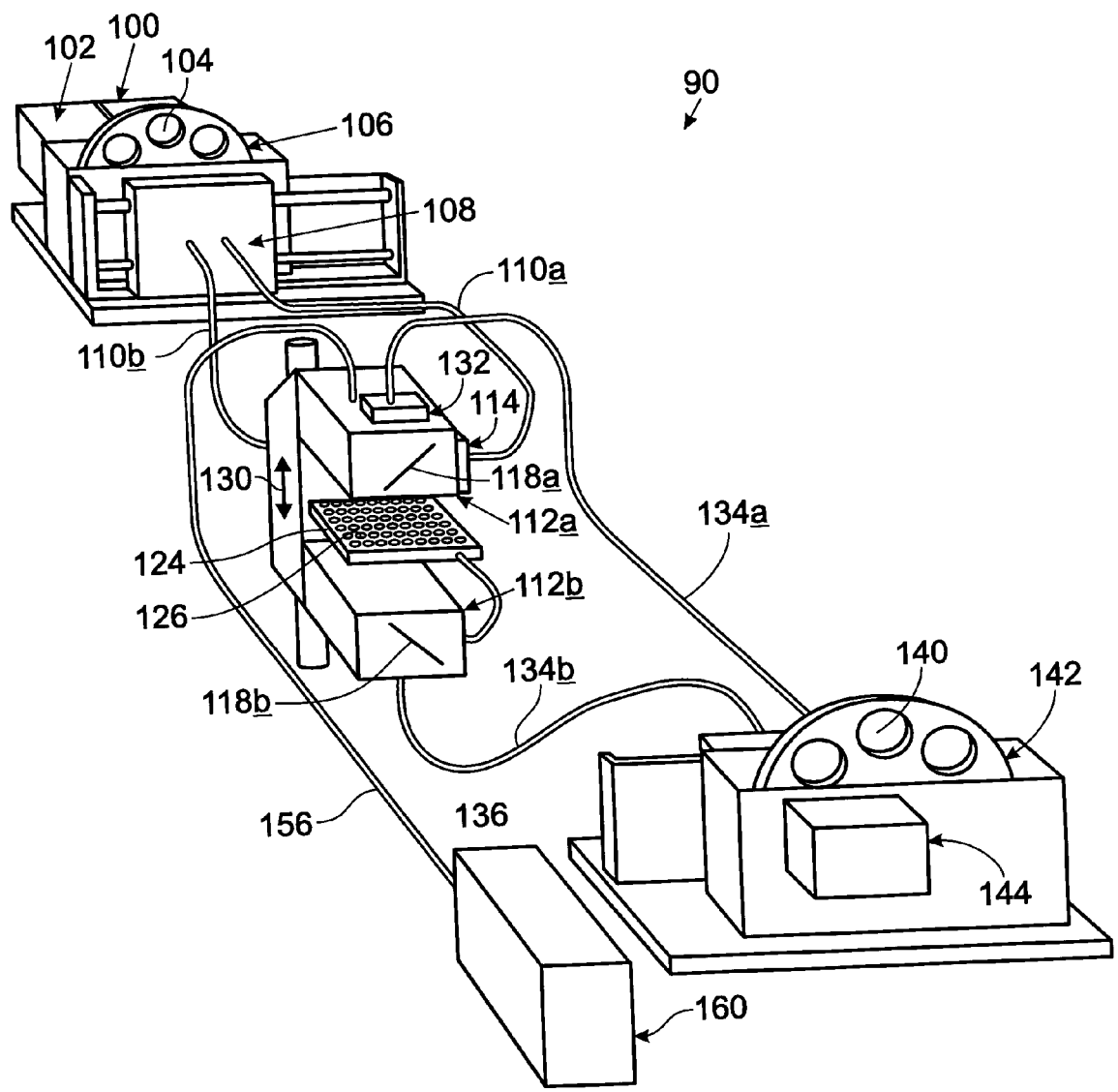
FIG. 4 is a partially schematic perspective view of the apparatus of FIG. 3.

The position of the sensed volume can be moved precisely within the composition to enhance or optimize the signal-to-noise and signal-to-background ratios. For example, the sensed volume may be moved away from walls in the sample holder to optimize signal-to-noise and signal-to-background ratios, reducing spurious signals that might arise from luminophores bound to the walls and thereby immobilized. In apparatus 90, position in the X,Y-plane perpendicular to the optical path is controlled by moving the stage supporting the composition, whereas position along the Z-axis parallel to the optical path is controlled by moving the optics heads using a Z-axis adjustment mechanism 130, as shown in FIGS. 3 and 4. However, any mechanism for bringing the sensed volume into register or alignment with the appropriate portion of the composition also may be employed.

The combination of top and bottom optics permits assays to combine: (1) top illumination and top detection, or (2) top illumination and bottom detection, or (3) bottom illumination and top detection, or (4) bottom illumination and bottom detection. Same-side illumination and detection (1) and (4) is referred to as "epi" and is preferred for photoluminescence assays. Opposite-side illumination and detection (2) and (3) is referred to as "trans" and is preferred for absorbance assays. In apparatus 90, epi modes are supported, so the excitation and emission light travel the same path in the optics head, albeit in opposite or anti-parallel directions. However, trans modes also could be supported and would be helpful for absorbance assays. Generally, top optics can be used with any sample holder having an open or transparent top, and bottom optics can be used with sample holders having optically transparent bottoms, such as glass or thin plastic bottoms.

Light is transmitted by the composition in multiple directions. A portion of the transmitted light will follow an emission pathway to a detector. Transmitted light passes through lens 117c and may pass through an emission aperture 131 and/or an emission polarizer 132. In apparatus 90, the emission aperture is placed in an image plane conjugate to the sensed volume and transmits light substantially exclusively from this sensed volume. In apparatus 90, the emission apertures in the top and bottom optical systems are the same size as the associated excitation apertures, although other sizes also may be used. The emission polarizers are included only with top optics head 112a. The emission aperture and emission polarizer are substantially similar to their excitation counterparts. Emission polarizer 132 may be included in detectors that intrinsically detect the polarization of light.

Excitation polarizers 114 and emission polarizers 132 may be used together in nonpolarization assays to reject certain background signals. Luminescence from the sample holder and from luminescent molecules adhered to the sample holder is expected to be polarized, because the rotational mobility of these molecules should be hindered. Such polarized background signals can be eliminated by "crossing" the excitation and emission polarizers, that is, setting the angle between their transmission axes at 90°. As described above, such polarized background signals also can be reduced by moving the sensed volume away from walls of the sample holder. To increase signal level, beamsplitter 118 should be optimized for reflection of one polarization and transmission of the other polarization. This method will work best where the luminescent molecules of interest emit relatively unpolarized light, as will be true for small luminescent molecules in solution.

Transmitted light next passes through an emission fiber optic cable 134a,b to an emission optical shuttle (or switch) 136. This shuttle positions the appropriate emission fiber optic cable in front of the appropriate detector. In apparatus 90, these components are substantially similar to their excitation counterparts, although other mechanisms also could be employed.

Light exiting the fiber optic cable next may pass through one or more emission "intensity filters," which generally comprise any mechanism for reducing the intensity of light. Intensity refers to the amount of light per unit area per unit time. In apparatus 90, intensity is altered by emission neutral density filters 138, which absorb light substantially independent of its wavelength, dissipating the absorbed energy as heat. Emission neutral density filters 138 may include a high-density filter H that absorbs most incident light, a medium-density filter M that absorbs somewhat less incident light, and a blank O that absorbs substantially no incident light. These filters are changed by hand, although other methods also could be employed, such as a filter wheel. Intensity filters also may divert a portion of the light away from the sample without absorption. Examples include beam splitters, which transmit some light along one path and reflect other light along another path, and Pockels cells, which deflect light along different paths through diffraction.

Light next may pass through an emission interference filter 140, which may be housed in an emission filter wheel 142. In apparatus 90, these components are substantially similar to their excitation counterparts, although other mechanisms also could be employed. Emission interference filters block stray excitation light, which may enter the emission path through various mechanisms, including reflection and scattering. If unblocked, such stray excitation light could be detected and misidentified as photoluminescence, decreasing the signal-to-background ratio. Emission interference filters can separate photoluminescence from excitation light because photoluminescence has longer wavelengths than the associated excitation light. Luminescence typically has wavelengths between 200 and 2000 nanometers.

The relative positions of the spectral, intensity, polarization, and other filters presented in this description may be varied without departing from the spirit of the invention. For example, filters used here in only one optical path, such as intensity filters, also may be used in other optical paths. In addition, filters used here in only top or bottom optics, such as polarization filters, may also be used in the other of top or bottom optics or in both top and bottom optics. The optimal positions and combinations of filters for a particular experiment will depend on the assay mode and the composition, among other factors.

Light last passes to a detector, which is used in absorbance and photoluminescence assays. In apparatus 90, there is one photoluminescence detector 144, which detects light from all photoluminescence modes. A preferred detector is a photomultiplier tube (PMT). Apparatus 90 includes detector slots 145*a–d* for four detectors, although other numbers of detector slots and detectors also could be provided.

More generally, detectors comprise any mechanism capable of converting energy from detected light into signals that may be processed by the apparatus, and by the processor in particular. Suitable detectors include photomultiplier tubes, photodiodes, avalanche photodiodes, charge-coupled devices (CCDs), and intensified CCDs, among others. Depending on the detector, light source, and assay mode, such detectors may be used in a variety of detection modes. These detection modes include (1) discrete (e.g., photon-counting) modes, (2) analog (e.g., current-integration) modes, and/or (3) imaging modes, among others, as described below.

The detection system further may include an identification system for automatically identifying removable optical elements installed in the device, for example, as described in U.S. Provisional Patent Application Ser. No. 60/383,311, filed May 22, 2002, which is incorporated herein by reference in its entirety for all purposes. Exemplary optical components include beam splitters (including 50:50 and dichroic beam splitters), filters (including spectral (e.g., interference) filters, intensity (e.g., neutral density) filters, and the like), and/or reflective and/or refractive optics (e.g., mirrors and lenses, respectively), among others. More generally, this identification system may be used in any suitable optical device, together with, or independent of, the detection methods described herein.

II.B Chemiluminescence Optical System

FIGS. 3, 4, and 6 show the chemiluminescence optical system of analyzer 50. Because chemiluminescence follows a chemical event rather than the absorption of light, the chemiluminescence optical system does not require a light source or other excitation optical components. Instead, the chemiluminescence optical system requires only selected emission optical components. In analyzer 50, a separate lensless chemiluminescence optical system is employed, which is optimized for maximum sensitivity in the detection of chemiluminescence.

Generally, components of the chemiluminescence optical system perform the same functions and are subject to the same caveats and alternatives as their counterparts in the photoluminescence optical system. The chemiluminescence optical system also can be used for other assay modes that do not require illumination, such as electrochemiluminescence.

The chemiluminescence optical path begins with a chemiluminescent composition 120 held in a sample container 126. The composition and sample container are analogous to those used in photoluminescence assays; however, analysis of the composition involves measuring the intensity of light generated by a chemiluminescence reaction within the composition rather than by light-induced photoluminescence. A familiar example of chemiluminescence is the glow of the firefly.

Chemiluminescence light typically is transmitted from the composition in all directions, although most will be absorbed or reflected by the walls of the sample container. A portion of the light transmitted through the top of the well may be collected using a chemiluminescence head 150, as shown in FIG. 3, from which it follows a chemiluminescence optical pathway to a detector. The direction of light transmission through the chemiluminescence optical system is indicated by arrows. In other embodiments, chemiluminescence may be detected through a clear bottom (or even side) of the sample holder.

The chemiluminescence head includes a nonconfocal mechanism for transmitting light from a sensed volume within the composition. Detecting from a sensed volume reduces contributions to the chemiluminescence signal resulting from "cross talk," which is the collection of light or "pickup" from neighboring wells. The nonconfocal mechanism includes a chemiluminescence baffle 152, which includes rugosities 153 that absorb or reflect light from other wells. The nonconfocal mechanism also includes a chemiluminescence aperture 154 that further confines detection to a sensed volume.

Light next passes through a chemiluminescence fiber optic cable 156, which may be replaced by any suitable mechanism for directing light from the composition toward the detector. Fiber optic cable 156 is analogous to excitation and emission fiber optic cables 110*a,b* and 134*a,b* in the photoluminescence optical system. Fiber optic cable 156 may include a transparent, open-ended lumen that may be filled with fluid. This lumen would allow the fiber optic to be used both to transmit luminescence from a microplate well and to dispense fluids into the microplate well. The effect of such a lumen on the optical properties of the fiber optic could be minimized by employing transparent fluids having optical indices matched to the optical index of the fiber optic.

Light next passes through one or more chemiluminescence intensity filters, which generally comprise any mechanism for reducing the intensity of light. In analyzer 50, intensity is altered by chemiluminescence neutral density filters 158. Light also may pass through other filters, if desired.

Light last passes to a detector, which converts light into signals that may be processed by the analyzer. In analyzer 50, there is one chemiluminescence detector 160. This detector may be selected to optimize detection of blue/green light, which is the type most often produced in chemiluminescence. A preferred detection is a photomultiplier tube, selected for high quantum efficiency and low dark count at chemiluminescence wavelengths (400–500 nanometers).

II.C Housing

Figure 7:
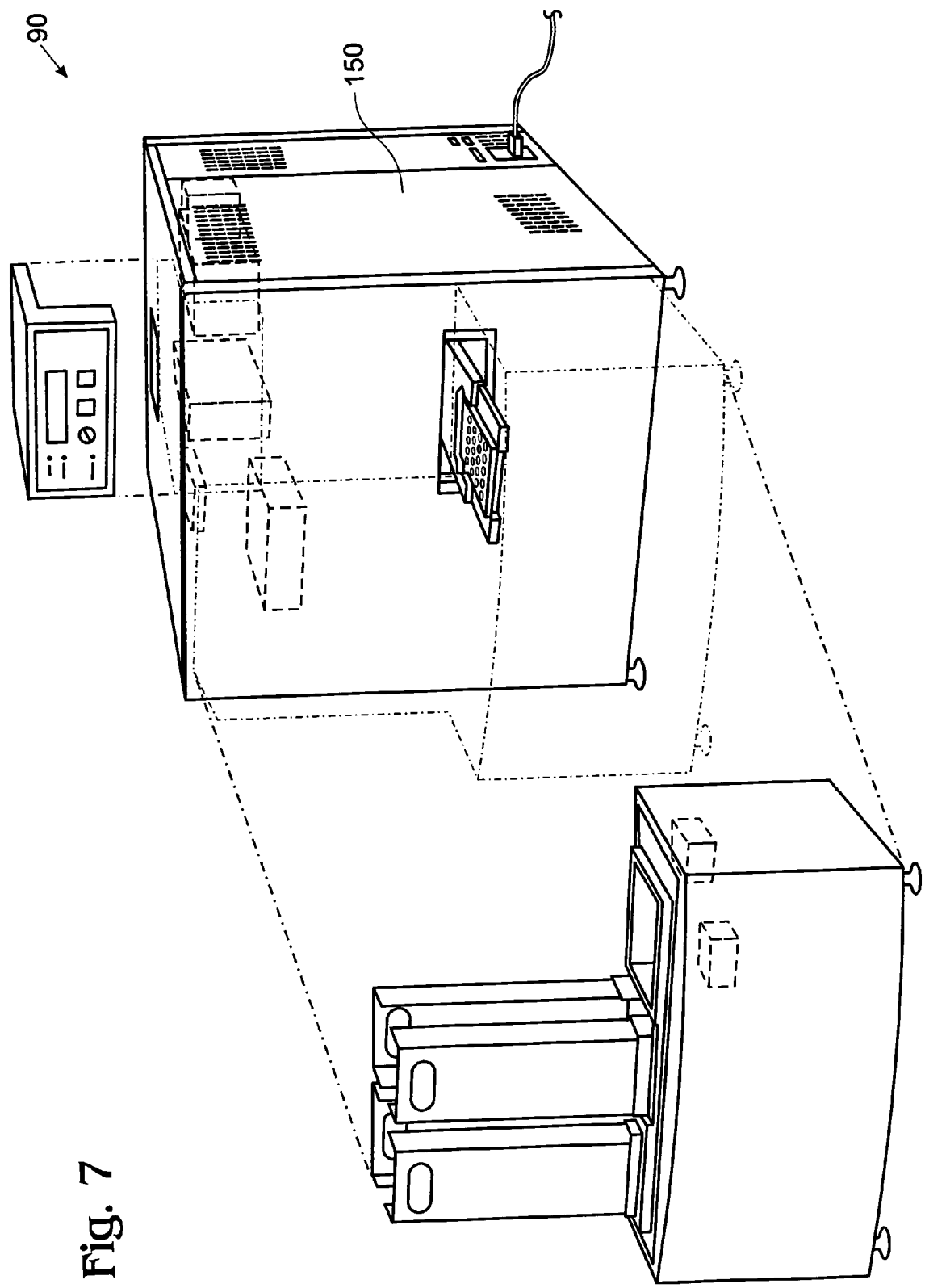
FIG. 7 is a partially exploded perspective view of a housing for the apparatus of FIGS. 3–6.

FIG. 7 shows a housing 150 and other accessories for the apparatus of FIGS. 3–6. Housing 150 substantially encloses the apparatus, forming (together with light source slots 103*a–d*) two protective layers around the continuous high color temperature xenon arc lamp. Housing 150 permits automated sample loading and switching among light sources and detectors, further protecting the operator from the xenon arc lamp and other components of the system.

II.D Alternative Apparatus

Figure 8:
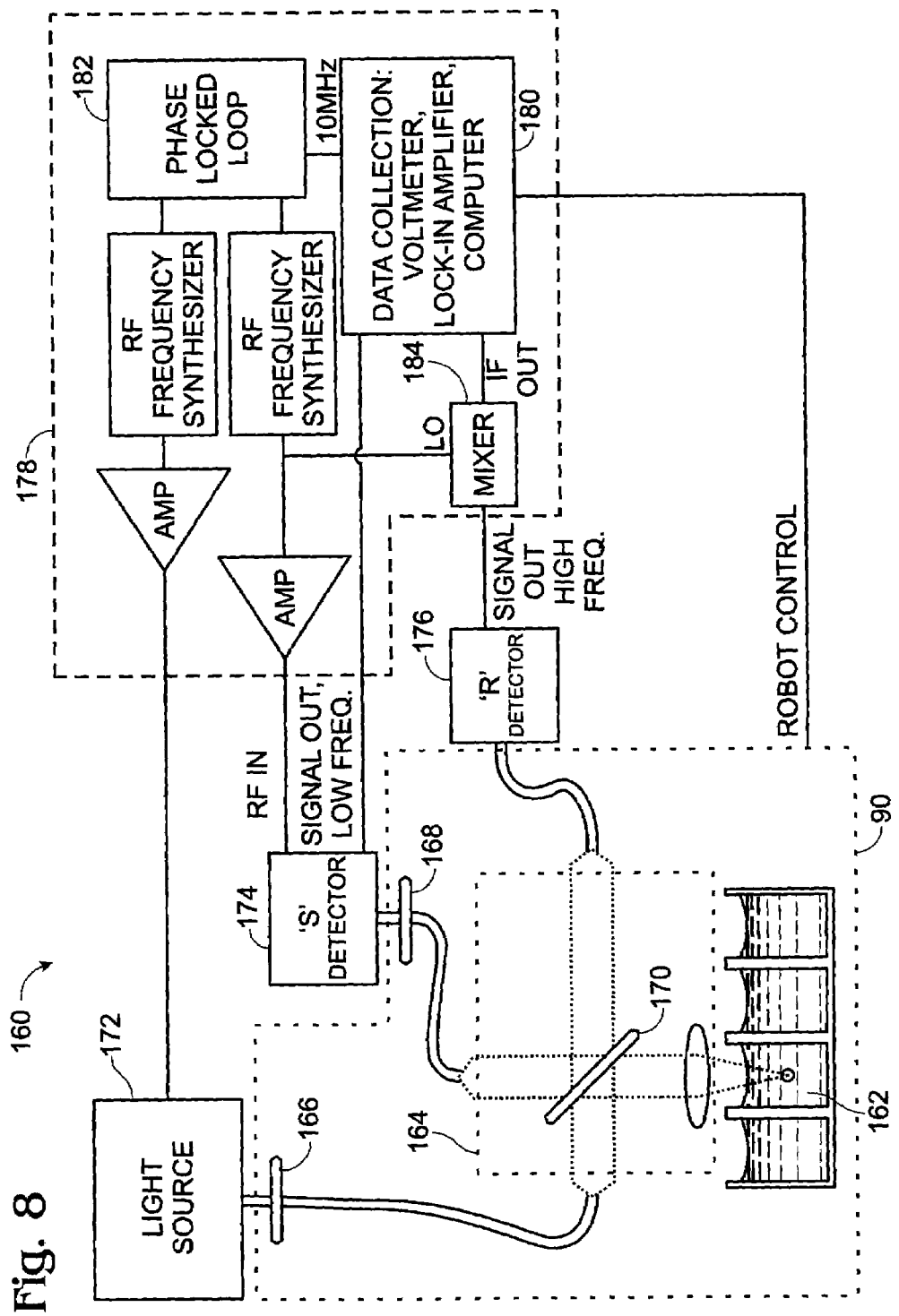
FIG. 8 is a schematic view of another apparatus for detecting light, in accordance with aspects of the invention.

FIG. 8 shows an alternative apparatus 160 for detecting light emitted by an analyte in a composition 162. Apparatus 160 includes substantial portions of apparatus 90, including its fiber-optic-coupled optics head 164, excitation 166 and emission 168 filters, dichroic beam splitter 170, and mechanisms for sample positioning and focus control. However, apparatus 160 also may include alternative light sources 172, alternative sample ('S') 174 and reference ('R') 176 detectors, and alternative detection electronics 178. In FIG. 8, alternative components 172–178 are shown outside apparatus 90, but they readily may be included inside housing 150 of apparatus 90, if desired.

Apparatus 160 may excite luminescence in various ways, such as using an LED or laser diode light source. For example, analytes absorbing blue light may be excited using a NICHIA-brand bright-blue LED (Model Number NSPB500; Mountville, Pa.). This LED produces broad-spectrum excitation light, so excitation filter 166 typically is used to block the red edge of the spectrum. If analytes are excited using a laser diode, an excitation filter is not necessary.

Apparatus 160 may detect luminescence and convert it to a signal in various ways. Luminescence can be detected using sample PMT 174, which may be an ISS-brand gain-modulated PMT (Champaign, Ill.). High-frequency luminescence can be frequency down-converted to a low-frequency signal using a technique called heterodyning. The phase and modulation of the low-frequency signal can be determined using a lock-in amplifier 180, such as a STANFORD RESEARCH SYSTEMS brand lock-in amplifier (Model Number SR830; Sunnyvale, Calif.). Lock-in amplifier 180 is phase locked using a phase-locked loop 182 to the modulation frequency of light source 172. To correct for drift in the light source, the output of light source 172 may be monitored using reference PMT 176, which may be a HAMAMATSU-brand PMT (Model Number H6780; Bridgewater, N.J.). If reference PMT 176 can respond to high-frequency signals, the heterodyning step can be performed using an external mixer 184. The phase and modulation of reference PMT 176 also may be captured by lock-in amplifier 180 and used to normalize the signal from sample PMT 174.

A computer or processor controls the apparatus, including the external components. The computer also directs sample handling and data collection. Generally, phase and modulation data are collected at one or more frequencies appropriate for the lifetime of the analyte. In some cases, phase and modulation may be measured at one or a few frequencies and processed by the computer or processor to help reduce detected background.

II.E Methods

Apparatus 90 and apparatus 160 both may be used to conduct a variety of steady-state and time-resolved luminescence assays. Steady-state assays measure luminescence under constant illumination, using the continuous light source, or, in some embodiments, by averaging using a time-varying source. Time-resolved polarization assays measure luminescence as a function of time, using either the continuous light source, with its intensity appropriately modulated, or the time-varying light source.

Intensity assays may be conducted by monitoring the intensity of the luminescence emitted by the composition.

Polarization assays may be conducted as follows. Excitation light from the continuous light source is directed through an excitation filter, low-luminescence fiber optic cable, and excitation polarization filter. Excitation light then is directed to a beamsplitter, which reflects most of the light onto a composition and transmits a little of the light into a light monitor. Emitted light from the composition is directed back through the beamsplitter and then is directed through another low-luminescence fiber optic cable, an emission filter, and a polarization filter (in either the S or P orientation) before detection by a photomultiplier tube. Two measurements are performed for each composition, one with excitation and emission polarizers aligned and one with excitation and emission polarizers crossed. Either polarizer may be static or dynamic, and either polarizer may be set in the S or P orientation, although typically the excitation polarizer is set in the S orientation.

Additional optical assays may be conducted using procedures outlined in the patents, patent applications, and other materials incorporated by reference above and/or generally known to persons of ordinary skill in the art. Such additional assays include, among others, absorption, scattering, reflection, fluorescence lifetime (FLT), total internal reflection fluorescence (TIRF), fluorescence correlation spectroscopy (FCS), and fluorescence recovery after photobleaching (FRAP), and analogs based on phosphorescence and/or other electronic transitions.

III. Detection Modes

This section describes exemplary systems, including apparatus and methods, for detecting light, in accordance with aspects of the invention. These systems may have a variety of advantages, including improved use of incoming light and/or detection time, among others. These systems are widely applicable, for various devices (e.g., flash or continuous light source, chemical or electrochemical source, analog or digital detector, etc.), for a variety of assays (e.g., absorption, photoluminescence (intensity, polarization, energy transfer, ratiometric, etc.), chemiluminescence, etc.), for a variety of sample holders (e.g., microplates, microarrays, biochips, cuvettes, etc.). These and other aspects of the detection systems are described herein, including, among others, (I–IV) detection devices, and (V–VI) detection strategies.

III.A Detection Device 1

Figure 9:
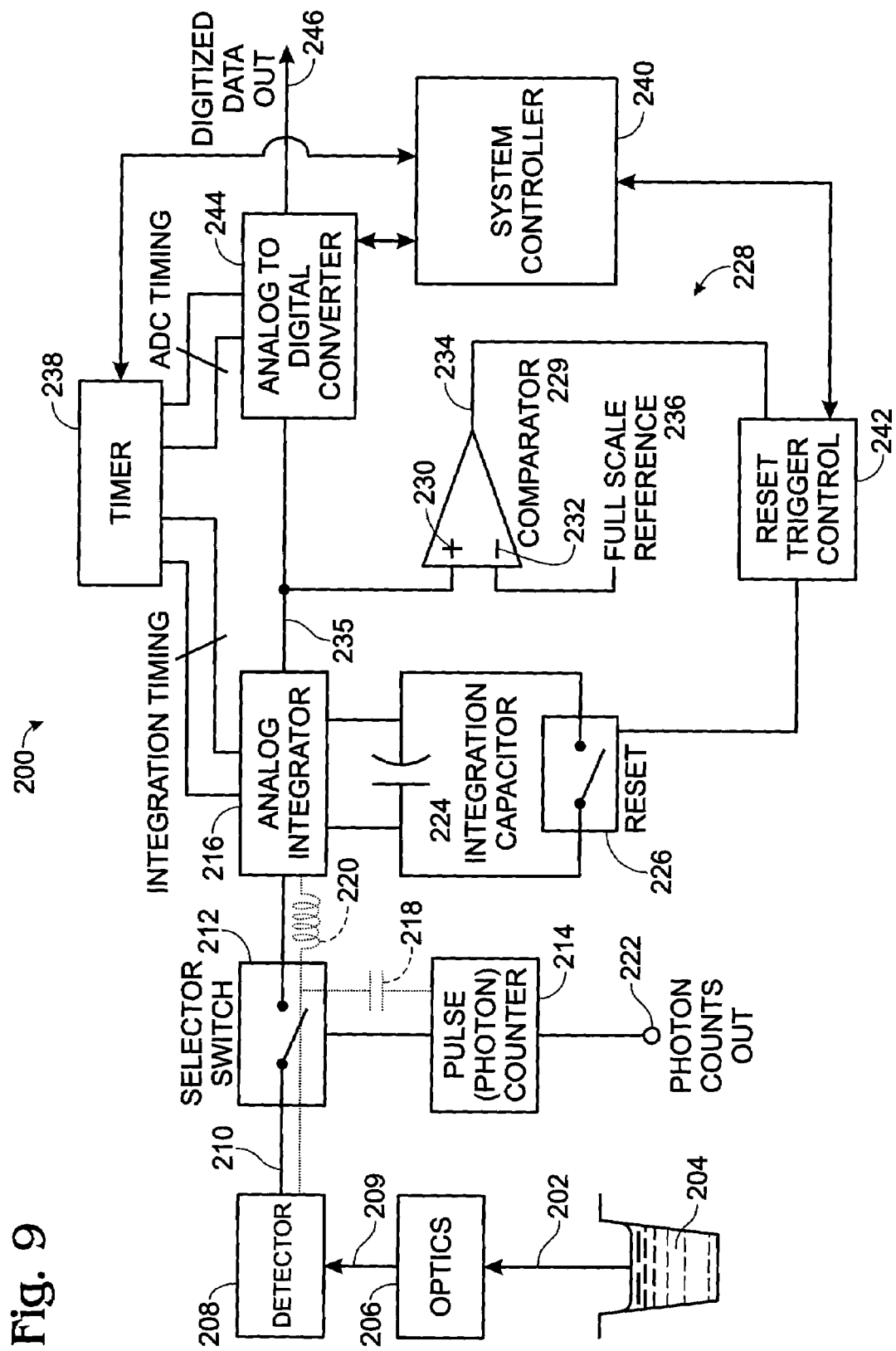
FIG. 9 is a block diagram of yet another apparatus for detecting light, in accordance with aspects of the invention.

FIG. 9 is a block diagram showing a first exemplary device 200 for detecting light, in accordance with aspects of the invention. Here, light 202 leaving a composition 204 may be directed by appropriate optics 206 to a detector 208. Optics 206 and detector 208 may take various forms, including forms shown in FIGS. 3–8 and described above. Generally, detector 208 has an input 209 that receives light and an output 210 that corresponds to the received light.

Output 210 may take various forms, including current and/or voltage signals. For example, depending on the intensity of the light received by the detector, the output may be discrete pulses corresponding to individual photons and/or an analog voltage or current proportional to the intensity of the incident light. In device 200, output 210 is directed through a selector switch 212, which selectively routes the output toward various detection components, including a pulse (photon) counter 214 and an analog integrator 216. Selector switch 212 may be manual, permitting a user to select between detection components. Alternatively, or in addition, selector switch 212 may be passive, allowing use of both detection components based on the intensity of light and/or the type of assay, among others. A passive selector switch may be constructed by omitting switch 212 and connecting a capacitor 218 from the output of the detector to pulse counter 214, and an inductor 220 from the output of the detector to analog integrator 216. Capacitor 218 will ass AC components of output 210 to pulse counter 214, while inductor 220 passes the C component of output 210 to analog integrator 216. Typical capacitances for capacitor 18 range between 1 and 10 nanoFarads, and typical inductances for inductor 220 range between 0.1 and 1 microHenrys. As another alternative, selector switch may be an electronically controlled switching device such as a solid-state switch or a relay, thereby allowing automatic control of the switch to accommodate expected or measured light levels.

Pulse counter 214 may be used as a discrete accumulator or integrator to monitor or sample the detected light by counting the number of photons in the detected light. Typically, a detector is chosen that generates an output corresponding to each detected photon. For example, photomultiplier tubes (PMTs) generate a current pulse for (at least essentially) each photon that strikes the photocathode in the PMT. The discrete output from the detector may be summed over a sampling period or integration time, and the amount of detected light may be reported in units of counts, counts/second, or relative fluorescence units (RFUs), among others, using an associated output port 222. These results may be corrected for fluctuations in light source intensity if they represent photoluminescence, using a reference detector as described above.

Analog integrator 216 may be used as an analog accumulator to monitor the detected light by generating a signal corresponding to the output of the detector. For example, current pulses from a PMT or other detector may be stored (integrated) using a capacitor 224 or other storage component in an electronic circuit. As the capacitor is charged, the analog voltage across the capacitor increases in proportion to the total number of photons collected by the PMT during the integration time. Typical capacitances range between 0.22 and 100 nanoFarads. Exemplary capacitors include low-leakage polystyrene and polyester capacitors to minimize drift error. Results from the analog integrator may be reported most naturally in RFUs; however, results also or additionally may be reported in terms of counts or counts/second. These results also may be corrected using a reference detector, if appropriate.

The size of capacitor 224 may be selected, manually or automatically, to optimize the precision and range of detection. Generally, the greatest precision is obtained with the smallest capacitor, and the greatest range is obtained with the largest capacitor. Capacitor rating is determined by total counts, not counts/second, because saturation is determined by total counts or its analog counterpart. For a continuous light source, the total number of counts may be expressed as the integral of the counts/second with respect to the integration time. For a flash lamp, the total number of counts may be expressed as the product of the counts per flash and the number of flashes. In use, the capacitor may be zeroed (e.g., using a reset 226) before each sampling period, and the capacitor may be charged to one-half to three-fourths full during each sampling period, with two-thirds full being a preferred value. To enhance flexibility, the apparatus may include a plurality of capacitors or other storage components, each with different capacities. Alternatively, or in addition, an amplifier or attenuator can be placed selectively between the detector output and integrator input to scale the output of the detector to a range that can be integrated without exceeding the capacity of the storage component for the expected light intensity. The output can be scaled to account for amplification or attenuation caused by the amplifier or attenuator, respectively.

The output signal from the integrator may be fed to a range monitoring device 228, which may include a threshold detection device in the form of operational amplifier or comparator 229. Comparator 229 may include a positive input 230, a negative input 232, and an output 234. Positive input 230 may be coupled to the output signal from the integrator. Negative input 232 may be connected to a full-scale range reference 236, such as a voltage reference. The reference may be adjustable over a range, for example, using a potentiometer configured as a voltage divider. The reference also may be fixed at a particular value, for example, using a Zener diode. The output of the comparator is low as long as the voltage at negative input 232 exceeds the voltage at positive input 230. However, when the integrator output signal voltage exceeds reference voltage 236, the output of the comparator will swing to high. Thus, by monitoring the output of the comparator, it is possible to detect if and when the reference value has been exceeded. The output signal of the integrator may be monitored in other ways as well, including digitally or with other analog circuitry.

The timing of detection may be specified and monitored in any suitable manner, for example, by using one or more timers 238 and system controllers 240. Before detecting light from a sample, system controller 240 may zero timer 238, and it further may zero analog integrator 216 using a trigger controller 242 and reset 226. After completing the sample period, system controller 240 may process the integrated signal stored on analog integrator 216 using an analog-to-digital converter 244, and output the data and the sampling time using an associated output port 246. Other mechanisms for preparing the analog integrator for data collection and for outputting data from the analog integrator after data collection also may be employed.

III.B Detection Device 2

Figure 10:
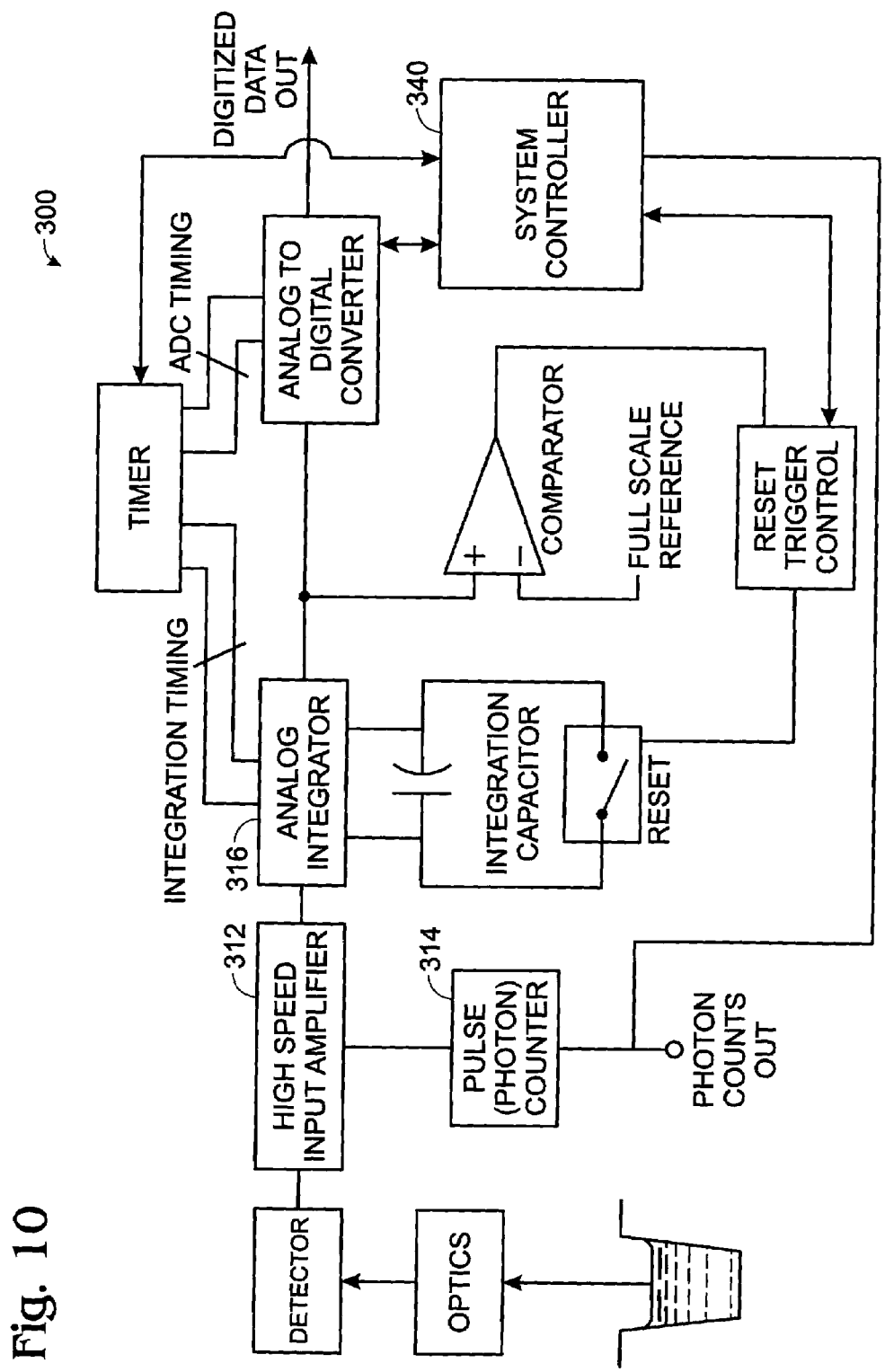
FIG. 10 is a block diagram of yet another apparatus for detecting light, in accordance with aspects of the invention.

FIG. 10 is a block diagram showing a second exemplary device 300 for detecting light, in accordance with aspects of the invention. Device 300 is similar to device 200 in FIG. 9, with a few exceptions. First, selector switch 212 in device 200 is replaced by a high-speed input amplifier 312 in device 300. High-speed input amplifier 312 preferably has accurate signal response from DC to 0.5 or 1 GHz AC, permitting simultaneous use of a pulse counter 314 and an analog integrator 316. Second, output from the pulse counter in device 300 is connected to a system controller 340, unlike in device 200. Together, these differences extend the range of device 300 relative to device 200, because device 300 may switch or choose automatically between the pulse counter and the analog integrator, as dictated by received light levels and/or the system controller.

III.C Detection Device 3

Figure 11:
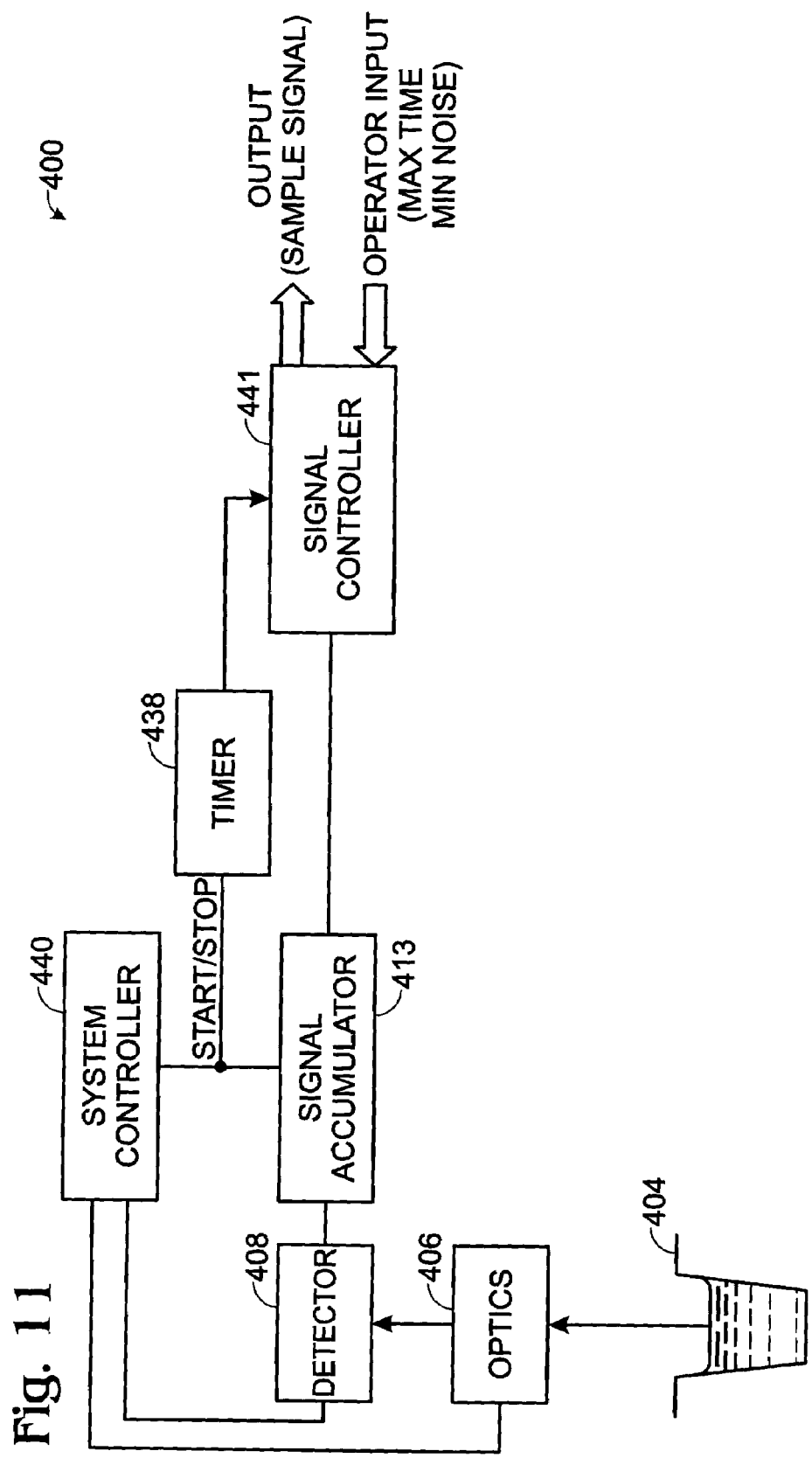
FIG. 11 is a block diagram of yet another apparatus for detecting light, in accordance with aspects of the invention.

FIG. 11 is a block diagram showing a third exemplary device 400 for detecting light, in accordance with aspects of the invention. This device is similar to those shown in FIGS. 9 and 10, with a few exceptions. First, device 400 converts into software functions many of the counting and comparison functions that are performed by hardware in devices 200 and 300. Second, device 400 includes a signal controller 441 that facilitates inputting criteria from an operator for terminating sampling, based on temporal and/or noise limitations, among others. However, despite these differences, device 400 still shares many features with devices 200 and 300, including optics 406 and a detector 408 for receiving light from a sample 404, an accumulator 413 (combining various functions from the other devices), a timer 438, and a system controller 440.

II.D Detection Device 4

Figure 12:
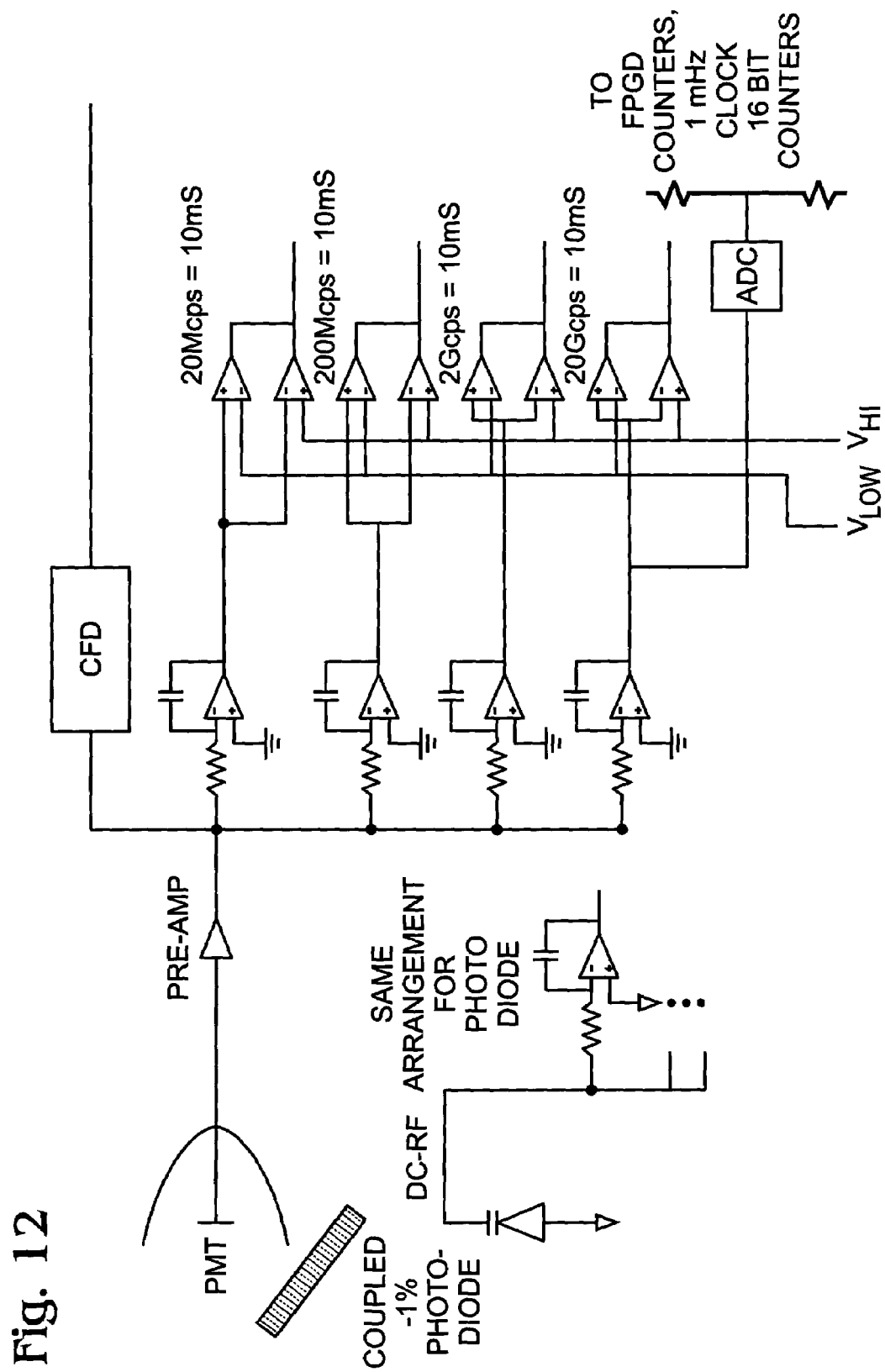
FIG. 12 is a schematic diagram of an integration section of yet another apparatus for detecting light, similar to the devices shown in FIGS. 9–11, with additional automatic range scaling.
Figure 13:
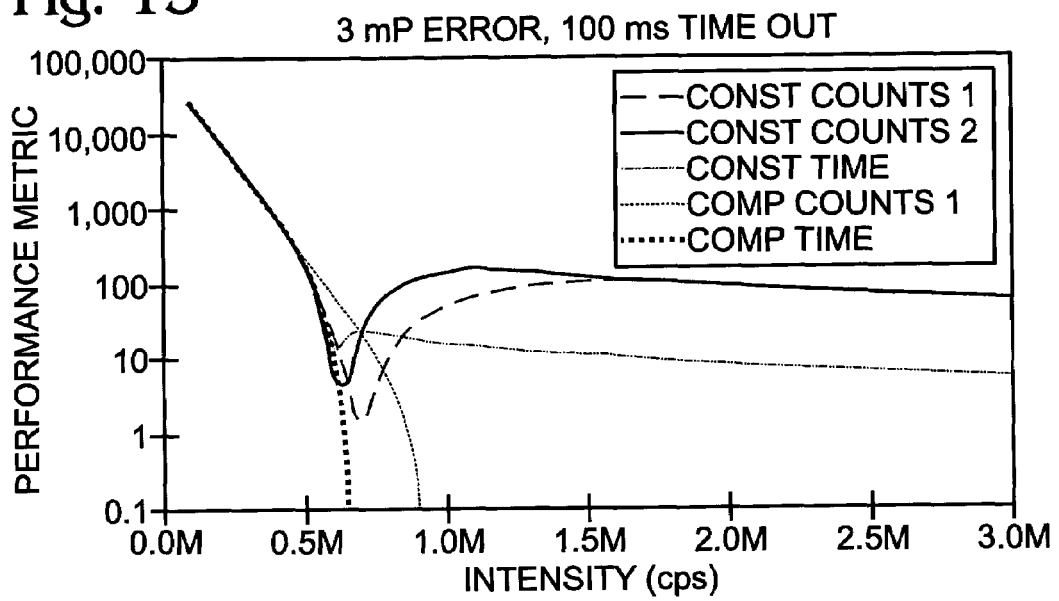
FIG. 13 is a graph of an exemplary performance metric versus intensity for polarization assays, illustrating the relative performances of fluorescence polarization detection methods 1–5, as described in Example 3.
Figure 14:
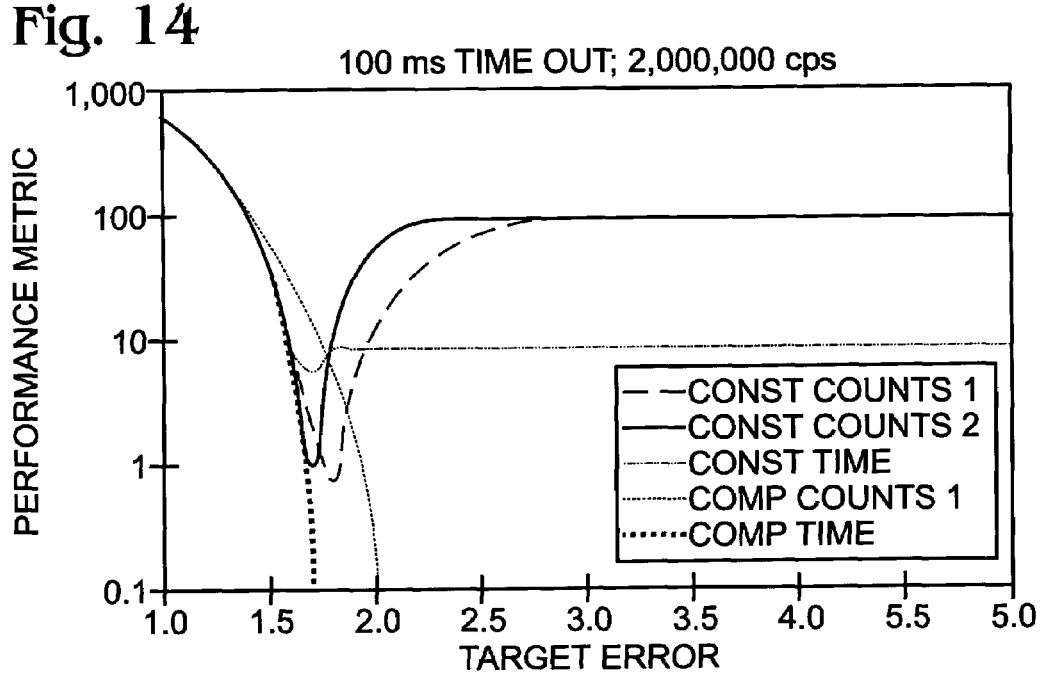
FIGS. 14–16 are graphs of an exemplary performance metric versus target error for polarization assays, illustrating the relative performances of fluorescence polarization detection methods 1–5, as described in Example 3.
Figure 15:
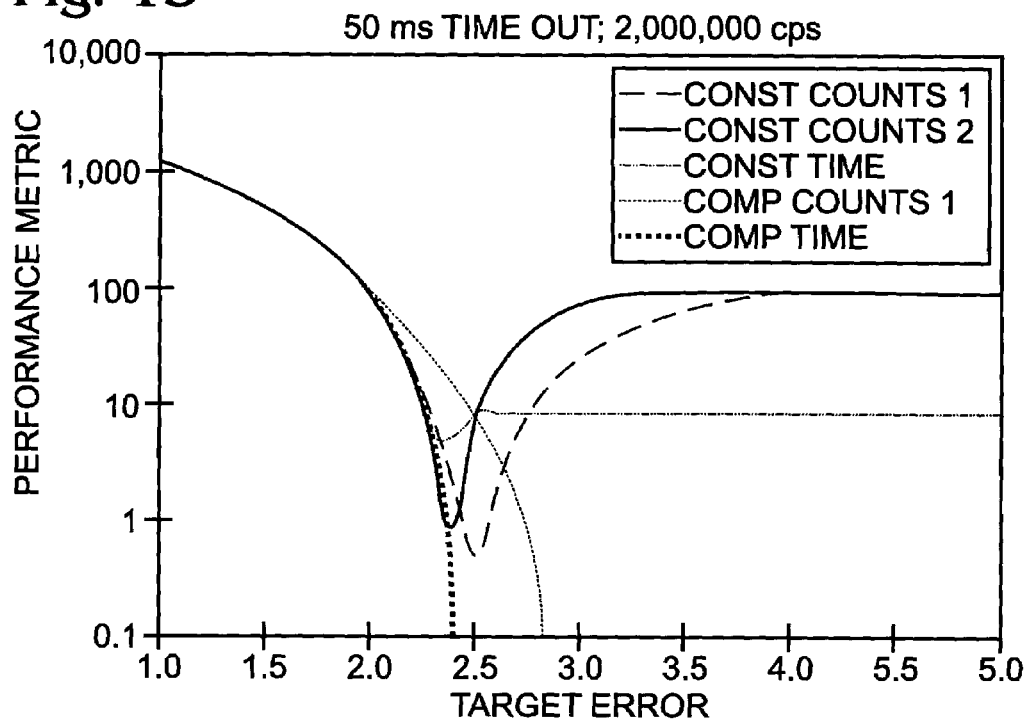
Figure 16:
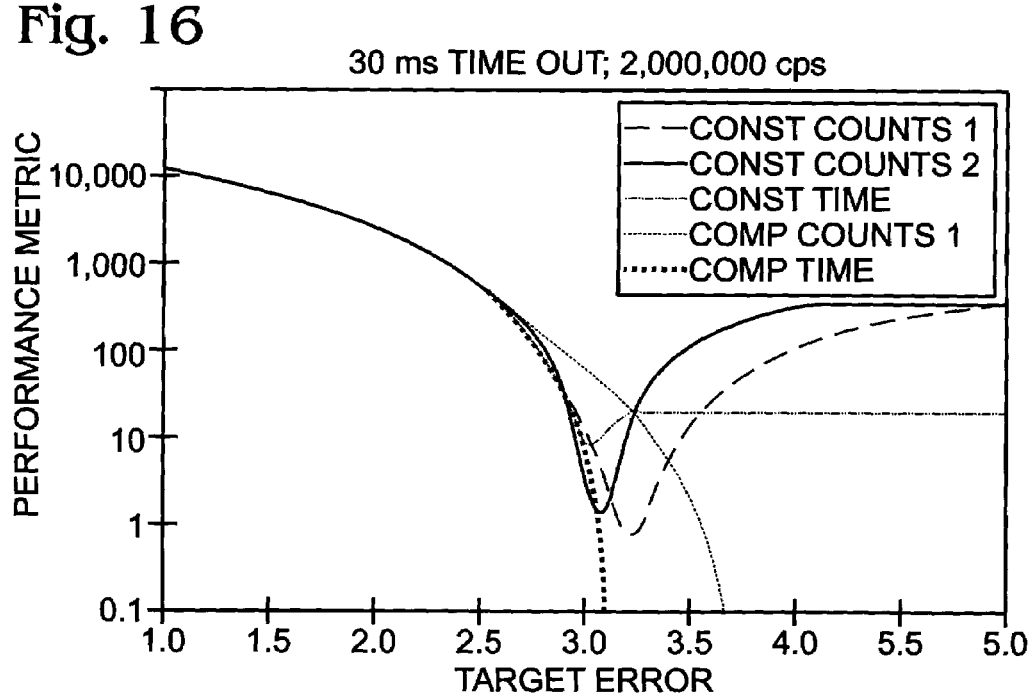

FIG. 12 is a schematic diagram showing an integration section of a fourth exemplary device for detecting light, in accordance with aspects of the invention. This device is similar to those shown in FIGS. 9–11; however, it may provide additional automatic range scaling.

The signal output from the PMT in FIG. 12 may be fed to a preamplifier that converts the current output from the PMT to a voltage output. This preamplifier preferably has good performance from DC to radio frequency AC, as described above.

The output of the preamplifier may be fed in parallel to a number of integration devices. Here, one integration device is a photon counter, which is useful for the lowest photon intensities. The other integration devices are four analog integrators, each having substantially identical construction, except for the size of the integration capacitor. In particular, the first three analog integrators each incorporate a capacitor that is about one order of magnitude smaller than the capacitor of the integrator that follows.

The output of each of the integration devices may be fed to a discriminator section, which monitors the output voltage between a preselected high and low voltage, $V_L$ and $V_H$, as illustrated. The output of the individual discriminator sections for each integration device may be used to trigger a counter corresponding to that integration device. Here, the counter for each integration device begins counting when the output from the corresponding integration device exceeds $V_L$, and stops counting when the output exceeds $V_H$. Thus, the counters can be used to determine the time required to saturate their associated integration devices. Thus, for a medium-intensity signal, the time required for the lowest range integration device to achieve saturation may be short relative to the overall sampling period. The time required for the next larger range integration device will be approximately an order of magnitude larger. The largest range integration devices may in fact not saturate during a particular sampling period with a medium intensity signal.

When computing a light intensity for a given sample period, it generally is preferable to select the output of an integration device that either recently saturated or was near to saturation. The signals from such devices, or the time required for saturation, as the case may be, will provide the most accurate basis for computing the intensity.

An advantage of this system is that an intensity value always can be computed based solely on the time to saturation for the largest range integration device that saturated. This can be accomplished by dividing the number of photons required for saturation by the time to saturation. If none of the analog integration devices saturated, the integrated signal from the counter can be used. Alternatively, the analog value of the integration device nearest to saturation but not yet having saturated can be measured with an analog-to-digital converter and used to compute the intensity.

To increase further the range of intensities that the device can measure, an additional type of detector (e.g., photodiode) can be used in parallel with the PMT. The output of the photodiode can be fed to a series of analog integrators, like those above. Thus, when the intensity exceeds that which a PMT can measure accurately, the photodiode will be in range.

The sample period may be terminated early if the user is satisfied when a predetermined number of photons are collected, as described above. Termination occurs when a corresponding integration signal has been achieved, as measured by the integration devices.

III.E Detection Strategies 1

The invention provides systems, including apparatus and methods, for improving light detection time. These improvements, in turn, may lead to higher throughput and/or higher precision in assays limited by shot noise and/or other considerations. The system may include collecting and monitoring the optical signal from an assay until a user-specified measurement signal (e.g., precision, total intensity, etc.) or a user-specified time is reached, whichever occurs first. The maximum time limit guarantees a minimal sample throughput, while the minimum signal (e.g., precision) allows the data collection system to increase throughput when adequate precision is achieved.

The termination criteria (termination measurement signal, termination time) generally may be set as desired, arbitrarily, or based on some predicted or measured parameter(s). This section includes exemplary methods for establishing target termination criteria based on a target measurement precision and/or an estimated assay result. These targets and estimates may be based on models of measurement noise and/or measurements of assay results. The measurements of assay results may be performed before running the assay and/or while running (an earlier portion of) the assay.

These and other aspects of the detection strategies are described below, including (1) an overview of selected detection devices and methods, and (2) a set of exemplary applications, relating to polarization assays.

III.E.1 Overview of Selected Detection Devices and Methods

The devices for detecting light may include a variety of components, including one or more of the following: (1) a detector configured to receive light from a sample; (2) an accumulator configured to generate an accumulator signal corresponding to the total light received by the detector from the sample during a sampling period; (3) a timer configured to measure elapsed time during the sampling period; and (4) a controller configured to terminate the sampling period after the accumulator signal reaches a predetermined accumulator value or after the elapsed time reaches a predetermined detection time limit, whichever occurs first.

The predetermined accumulator value may be calculated, for example, based on a target measurement precision. This target precision may be inputted in any suitable manner, including manually by an operator, or automatically by the device (e.g., by reading a barcode and/or looking it up in a database or lookup table). In some cases, the predetermined accumulator value further may be calculated based on a model of measurement noise, such as shot noise. Shot noise, sometimes referred to as photon noise or Poisson noise, is equal to the square root of the measurement value. In shot noise, or other cases, the predetermined accumulator value further may be calculated based on an estimated measurement result. This estimated result may be based on an expected result and/or a pre- or co-measured result, among others.

The device may be configured to receive light automatically and sequentially from a plurality of samples. These samples may be disposed at different positions in a microplate or a microarray. In some cases, the predetermined detection time limit may be calculated using a (user-inputted or otherwise available) maximum total time for receiving light from the plurality of samples. The device may be configured to receive light automatically from each of the plurality of samples during first and second sampling periods. The device may further comprise an automatic sample handler configured to advance samples for analysis, where the time between beginning to analyze successive samples is shorter if the accumulator signal reaches the predetermined accumulator value before the elapsed time reaches the predetermined detection time limit.

The device may be configured to receive light from the sample automatically during first and second sampling periods. These sampling periods may be sequential or at least partially or completely overlapping. In some cases, the device may include a second detector, where light associated with the first sampling period is received by one detector, and light associated with the second sampling period is received by the other detector. The device may include a controller configured to terminate the first and second sampling periods independently after an accumulator signal for each period reaches a predetermined accumulator value or after the elapsed time for each period reaches a predetermined detection time limit, whichever occurs first. Alternatively, or in addition, the controller may be configured such that the duration of the second sampling period is determined at least in part by the duration of the first sampling period. In this latter case, the controller may, among others, terminate the second sampling period such that it has at least substantially the same duration as the first sampling period, or terminate the second sampling period such that it has a duration equal to about twice the predetermined period minus the duration of the first sampling period. The device may be configured such that light received during the first and second sample periods is of at least substantially the same or substantially different wavelengths or polarizations. The device may include a processor configured to compute a quantity such as luminescence polarization or luminescence anisotropy related to the polarization of the light received during the first and second sampling periods. Alternatively, or in addition, the device may include a processor configured to compute a quantity related to a ratio of the light received during the first and second periods. In assays involving more than one sampling period, the predetermined accumulator values for may be the same or different for each sampling period.

The device may include an excitation source configured to excite emission of light from the sample. The source may be a light source for photoluminescence, a chemical reaction for chemiluminescence, and/or an electrical potential or current for electrochemiluminesce. The emitted light may have any wavelength, including but not limited to between about 200 nanometers and about 2000 nanometers, between about 250 nanometers and about 700 nanometers, and between about 400 nanometers and about 700 nanometers, among others.

The device may include a stage configured to support a microplate, a second detector configured to receive light from the sample; and/or a second accumulator configured to generate a second accumulator signal corresponding to the total light received by the second detector from the sample during a second sampling period. A second detector and accumulator may be particularly useful in assays in which the first and second sampling periods are at least partially overlapping.

The device may include a discrete and/or analog accumulator. A discrete accumulator may generate an accumulator signal by counting pulses from the detector corresponding to quanta of detected light. An analog accumulator may generate an accumulator signal by charging an integration capacitor, the charge on the capacitor corresponding to the amount of detected light. In the latter case, the accumulator may include a plurality of integration capacitors having substantially different capacities from one other, wherein the amount of detected light required to generate an accumulator signal equal to the predetermined accumulator value is selectable by choosing a particular one of the integration capacitors. Alternatively, or in addition, the accumulator also may include a discrete accumulator that accumulates the signal by counting pulses from the detector corresponding to quanta of detected light, wherein the device switches between the discrete and analog accumulators based on the amount of light detected. A digital accumulator may generate the accumulator signal by digitally measuring and summing the output of the detector at a plurality of discrete times during the sampling period. The device further may include a plurality of accumulators simultaneously operatively connected in parallel to the detector, each accumulator being configured to generate an integration value proportional to the integrated output of the detector during the sampling period, wherein the proportionality between the accumulator signal and the amount of detected light is substantially different for the different accumulators. In some cases, the device also may be able to report intensity in units selected from a group consisting of counts per unit time and relative luminescence units per unit time.

The device may be adapted to switch between digital and analog counting modes, depending on the amount of detected light.

The timer also may be discrete or continuous, casting elapsed time and detection time limits in terms of clock time or pulses (as of a flash lamp), among others. In constant time methods, the timer may specify the length of the measurement, at least substantially independent of a predetermined accumulator value.

The methods for detecting light may include a variety of steps, including one or more of the following: (1) detecting photons incident on a detector during a sampling period; (2) collecting data representative of the cumulative number of photons detected during the sampling period; and (3) terminating the sampling period when the cumulative number of photons detected during the sampling period reaches a predetermined threshold or a predetermined sample time expires, whichever occurs first.

The methods further may include (1) calculating the predetermined threshold based on a target measurement precision, (2) repeating the steps of detecting, collecting, and terminating for the same sample, and/or (3) repeating the steps of detecting, collecting, and terminating for a second sample.

The methods generally may use the detected light for any suitable purpose, including, among others, (1) computing a polarization, (2) computing a resonance energy transfer efficiency, and/or (3) computing a ratio.

III.E.2 Exemplary Applications

This section describes exemplary methods for performing polarization assays, based on predetermined termination criteria.

III.E.2.a Polarization Relations

Polarization may be defined in terms of parallel and perpendicular intensities, as described above in Section 1.B, and as reproduced below for convenience:

$$P = \frac{I_\| - I_\perp}{I_\| + I_\perp} \tag{6}$$

Here, P is the polarization value, $I_\|$ is the parallel intensity (e.g., counts/sec), and $I_\perp$ is the perpendicular intensity (e.g., counts/sec). The measured energy (E, e.g., counts) is related to the intensity (I) by the integration time (t):

$$E = I \cdot t \tag{7}$$

In these assays, the noise of collected (light) energy (e.g., the counts) is equal to the noise of the collected (light) intensity.

$$\frac{\sigma_E^2}{E^2} = \frac{\sigma_I^2}{I^2} \tag{8}$$

Here, E is the same as "Target Counts" below.

III.E.2.b Relation of Polarization Error and Intensity Errors

This section presents equations relating polarization error and intensity errors.

$$\frac{\delta P}{\delta I_\parallel} = \frac{2I_\perp}{(I_\parallel + I_\perp)^2} \tag{9a}$$

$$\frac{\delta P}{\delta I_\perp} = \frac{-2I_\parallel}{(I_\parallel + I_\perp)^2} \tag{9b}$$

$$\sigma_P^2 = \left(\frac{2I_\perp}{(I_\parallel + I_\perp)^2}\right)^2 \sigma_{I_\parallel}^2 + \left(\frac{-2I_\parallel}{(I_\parallel + I_\perp)^2}\right)^2 \sigma_{I_\perp}^2 \tag{10}$$

$$= \left(\frac{2I_\parallel I_\perp}{(I_\parallel + I_\perp)^2}\right)^2 \left[\left(\frac{\sigma_{I_\parallel}}{I_\parallel}\right)^2 + \left(\frac{\sigma_{I_\perp}}{I_\perp}\right)^2\right]$$

$$= \left(\frac{2I_\parallel I_\perp}{(I_\parallel + I_\perp)^2}\right)^2 \left[\left(\frac{\sigma_{E_\parallel}}{E_\parallel}\right)^2 + \left(\frac{\sigma_{E_\perp}}{E_\perp}\right)^2\right]$$

Here, $\sigma_P$ is polarization noise or precision, also referred to as the "Target Polarization Precision" below.

III.E.2.c Measures of Polarization

The parallel and perpendicular intensities have no predetermined relationship. However, for a given situation, there will be a relationship between these quantities, such as that expressed below, in Equation 11.

$$I_\parallel = I, \quad I_\perp = \alpha I \tag{11}$$

The ratio between the intensities, $\alpha$, is just another measure of the polarization as expressed by Equation 12.

$$P = \frac{1-\alpha}{1+\alpha}, \quad \alpha = \frac{1-P}{1+P} \tag{12}$$

III.E.2.d Constant Counts

This section describes results for "constant counts" methods, as illustrated below, in Example 3 (Methods 1, 2, and 5). Here, we assume that $E_\parallel = E_\perp = E$, and that the noise is shot noise:

$$\left(\frac{\sigma_{I_\parallel}}{I_\parallel}\right)^2 = \left(\frac{\sigma_{I_\perp}}{I_\perp}\right)^2 = \frac{1}{E} \tag{13}$$

The noise in P may be obtained by substituting Equation 13 into Equation 10 (with the aid of Equation 12), yielding the formula:

$$\sigma_P^2 = \frac{8\alpha^2}{(1+\alpha)^4} \frac{1}{E} = \frac{(1-P^2)^2}{2} \frac{1}{E} \tag{14}$$

This equation may be solved for E to arrive at a "complete constant counts" formula:

$$E = \frac{(1-P^2)^2}{2\sigma_P^2} \tag{15}$$

Equation 15 has a maximum when $\alpha=1$ (or, equivalently, $P=0$). This maximum may be used to estimate a worst-case termination criterion. Specifically, substituting and solving for E yields a "constant counts" formula:

$$E = \frac{1}{2\sigma_P^2} \tag{16}$$

III.E.2.e Constant Time

This section describes results for "constant time" methods, as illustrated below, in Example 3 (Methods 3 and 4). Here, we assume that $t_\parallel = t_\perp = t$, $E_\parallel = E$, and $E_\perp = \alpha E$, and that the noise is shot noise:

$$\left(\frac{\sigma_{I_\parallel}}{I_\parallel}\right)^2 = \frac{1}{E}, \quad \left(\frac{\sigma_{I_\perp}}{I_\perp}\right)^2 = \frac{1}{\alpha E} \tag{17}$$

The noise in P may be obtained, as done above for Equation 14:

$$\sigma_P^2 = \frac{4\alpha}{(1+\alpha)^3} \frac{1}{E} = \frac{(1-P)(1+P)^2}{2} \frac{1}{E} \tag{18}$$

Equation 18 may be solved for E to yield a "complete constant time" formula:

$$E = \frac{(1-P)(1+P)^2}{2} \frac{1}{\sigma_P^2} \tag{19}$$

Equation 19 has a maximum when $\alpha=\frac{1}{2}$ (or, equivalently, $P=\frac{1}{3}$). This maximum may be used to estimate a worst-case termination criterion. Specifically, substituting and solving for E yields a "constant time" formula:

$$E = \frac{16/27}{\sigma_P^2} \tag{20}$$

III.F Detection Strategies 2

The sampling or read time in the devices described above may be determined in several ways. First, the device may be instructed to integrate the detector output for a predetermined (fixed) time, as determined by the system controller and/or the timer. Second, the device may be instructed to integrate the detector output until a predetermined (fixed) integrated signal is obtained, as determined by the comparator and the value of the full-scale reference. Third, the device may be instructed to integrate the detector output either for a predetermined (fixed) time or until a predetermined (fixed) integrated signal is obtained, whichever comes first.

Fixed-time and fixed-signal detection modes may be used to provide overflow protection and/or to extend dynamic range beyond that available with discrete or analog detection alone. In analog detection, information may be lost if the integration capacitor or other storage component reaches its full-range value before the sampling period ends, even though the PMT or other detector was not saturated. This loss arises because the electronic circuit in analog counting cannot respond to signals above the full-scale count for each capacitor setting. Thus, with standard analog detection, each sample brighter than the saturation level will give an identical full-scale result.

The invention permits the intensity of detected light to be determined even if the integrated signal for the entire sample period would substantially exceed the storage capacity of the capacitor. The intensity of light may be expressed as an amount of light per unit time. Here, the time required to charge the storage component fully may be measured by a timer operatively associated with the comparator. Thus, if the capacitor reaches full charge prior to the end of the sample period, the intensity may be determined by relating the storage capacity of the capacitor to the amount of light detected by the detector, and then dividing that amount by the elapsed time in the sample period before reaching full charge. However, if the capacitor does not reach full charge during the sampling period, then the intensity may be determined using the actual charge and the sampling period.

Fixed-time and fixed-signal detection modes also may be used to reduce read time and/or to provide underflow protection. Generally, optical assays are affected by various sources of error, including photon noise (PN) and pipetting error (PE), among others. The coefficient of variation (CV) associated with the results of an optical assay affected by such sources of error might be represented by the formula:

$$CV_{assay} = \sqrt{CV_{PN}^2 + CV_{PE}^2} \tag{21}$$

Here, $CV_{PN} = (\text{\# detected photons})^{-1/2}$, and CVPE typically is in the range of 1–5%. Thus, to obtain a result that is limited by pipetting error, it is necessary only to collect enough photons to reduce $CV_{PN}$ to about 0.5–1%. This noise level corresponds to collecting between 10,000 and 20,000 photons. In many assays, good results may be obtained by collecting about this number of photons. For example, in fluorescence polarization assays, the polarization noise in millipoise (mP) is given by:

$$\text{Polarization noise} = \frac{1000}{\sqrt{2(\text{\# detected photons})}} \tag{22}$$

Polarization assays generally require polarization noise to be less than about 10 mP, corresponding to collecting at least about 5,000 photons. This equation is the same as Equation 16 (above) and Equation 26 for constant counts, solved for noise.

Total read time may be reduced by allowing the sample read time to vary as a function of signal strength, so that samples are analyzed just long enough to obtain a result that is not limited by the amount of light detected. For discrete detection, the pulse counter may be configured to count pulses only until a predetermined number or threshold of pulses is counted. For analog detection, the analog integrator may be configured to integrate the detector output until a preset threshold is achieved, where the threshold corresponds to collection of a predetermined amount of light. Specifically, the integrator may be zeroed, and the time required for the integrated detector current to trip the comparator may be measured. The integration time is a representation of the number of photons collected and hence the signal level.

The integrated detector current necessary to trip the comparator may be changed by changing the electronic gain, the threshold voltage, and/or the integration capacitor, among others. Such a change in comparator trip value will correspond to a change in the number of photons that can be collected (and in the associated signal-to-noise value). To increase the number of photons collected, a larger capacitor and/or a lower gain may be employed. Conversely, to decrease the number of photons collected, a smaller capacitor and/or a shorter time-out period may be employed.

Generally, the desired amount of light (number of photons) will be acquired quickly if the sample is bright and slowly if the sample is dim. If the sample is so dim that the desired number of photons cannot be collected within a preset time limit or timeout period, an underflow occurs. In this case, the measurement is deemed to have "timed out," and the integrator voltage may be measured by an analog-to-digital converter, and/or set to zero or another convenient value representing an underflow condition. Alternatively, if analog integration and photon-counting are performed simultaneously, the counter output determined in photon-counting mode may be used to determine intensity.

Table I shows the reduction in read times possible using variable-time reading, assuming that the reading time may be reduced from 100 milliseconds to 1 millisecond per sample. Reductions in read time become significant if numerous samples must be analyzed. For example, in high-throughput screening applications, samples may be housed in microplates that each contain 96, 384, or 1536 samples. Moreover, high-throughput screening applications typically require analyzing many such microplates.

TABLE I

| Plate Format | 96-well | 384-well | 1536-well |
| --- | --- | --- | --- |
| Move time + fixed read time | 43.2 sec | 115.2 sec | 307.2 sec |
| Move time + variable read time | 33.7 sec | 77.2 sec | 155.1 sec |
| Time saved per plate | 9.5 sec | 38.0 sec | 152.1 sec |
| Time savings (percent) | 23% | 33% | 49.5% |

The read time per microplate may be reduced using the savings in read time per sample, as shown with model data in Table I. Alternatively, the read time per microplate may be held constant, independent of the read time per sample, if desired. The latter option may be useful if microplate analysis is coupled to other processes that occur at fixed time intervals.

Table II shows exemplary guidelines for selecting suitable counting options and units, based on the assay, light source (if applicable), detector, and light intensity. These guidelines were developed for the embodiment shown in FIGS. 3–6 and 9; however, they apply in whole or part to similar systems. The guidelines assume, in appropriate part, that there are separate chemiluminescence and photoluminescence optical systems, and that there is selectable photon counting or analog integration, with a comparator associated with the analog detection.

TABLE II

|  | Discrete Counter | Analog Integrator | Comparator Option |
|---|---|---|---|
| Chemiluminescence | Optimal performance | Not applicable | Not applicable |
| Fluorescence Intensity (FI) (w/ continuous lamp) Units = cps | Low level signals <1.0 M cps | Higher signals or increase in dynamic range compared to digital | Optimal performance (with appropriate capacitor selection, good sensitivity and largest dynamic range) |
| Fluorescence Polarization (FP) (w/ continuous lamp) Units = cps | Low level signals <1.0 M cps | Higher signals or increase in dynamic range compared to digital | Optimal performance (with appropriate capacitor selection, good sensitivity and largest dynamic range) |
| Time-Resolved Fluorescence (TRF) (w/ flash lamp) Units = counts or cps | Optimal performance Low signal levels <1.0 M cps | Higher signals or increase in dynamic range (useful sensitivity settings 3 or 4) | Not recommended |
| Fluorescence intensity (w/ flash lamp) Units = counts | Not recommended (limited utility at the very lowest signal levels) | Optimal performance (with appropriate capacitor selection) | Not recommended |
| Fluorescence Polarization (w/ flash lamp) Units = counts | Not recommended (limited utility at the very lowest signal levels) | Optimal performance (with appropriate capacitor selection) | Not recommended |

Discrete (photon) counting generally trades dynamic range for sensitivity at very low signal levels. Saturation (e.g., ~1 million counts/second) is determined by the rate at which the detector and counting circuit receive photons. Discrete counting may be particularly advantageous for low-intensity detection in chemiluminescence and time-resolved fluorescence assays.

Analog counting (PMT current integration) generally trades sensitivity at the lowest signal levels for increased dynamic range. Saturation in analog counting typically occurs at much higher count rates (e.g., ~0.5–1 billion counts/second) than in discrete counting. The maximum integrable signal usually is determined by the size of the integration capacitor. Analog counting may be particularly advantageous for fluorescence intensity and fluorescence polarization assays conducted using a flash lamp.

Comparator counting (analog+time to full scale) generally trades sensitivity at the lowest signal levels for the largest dynamic range with a single instrument setting. Saturation is similar to that stated for analog counting. In contrast to purely analog counting, at high signal levels the "comparator" circuit detects when the capacitor is fully charged and automatically measures the time taken for the capacitor to reach full scale. Comparator counting may be particularly advantageous for low-intensity detection and dynamic range readings for fluorescence intensity and fluorescence polarization assays using a continuous lamp.

IV. EXAMPLES

The following examples are included for illustration and are not intended to limit or define the entire scope of the invention. Some of these examples refer to or make use of photon counts (e.g., in the integration targets). These counts may be provided, among others, by discrete detection systems that count photons explicitly and/or by analog detection systems that have known conversions to photon counts.

IV.A Example 1

Photoluminescence Intensity Assays Using a Continuous Light Source or Chemiluminescence Assays This example describes systems for performing, among others, chemiluminescence assays and photoluminescence intensity assays using a continuous light source.

The end-user configures the instrument with a Target Precision (CV) and a Detection Time Limit. The Detection Time Limit allows the user to maintain a minimal throughput, even if the sample has low intensity. The detection system software then converts the Target Precision to Target Counts, using the shot noise definition, by the algorithm:

$$\text{Target Counts} = \frac{1}{(\text{Target } CV)^2} \quad (23)$$

Here, Target CV is expressed as a fraction. The detection system then measures the sample until either the Target Counts or the Detection Time Limit is achieved. For example, if the end user requests a Target Precision of 3% (0.03) and a Detection Time Limit of 0.100 seconds, the detection system will measure the sample until about 1,100 counts are recorded or until 0.100 seconds elapses, whichever occurs first.

IV.B Example 2

Photoluminescence Intensity Assays Using a Flashed Light Source

This example describes systems for performing, among others, photoluminescence intensity assays using a continuous light source.

The end-user configures the instrument with a Target Precision (CV) and a Detection Time Limit, as with the continuous light source. The Detection Time Limit again allows the user to maintain a minimal throughput, even if the sample has low intensity. The detection system software then converts the Target Precision to Target Counts, again using the shot noise definition, by the algorithm:

$$\text{Target Counts} = \frac{1}{(\text{Target } CV)^2} \quad (24)$$

Here, Target CV is expressed as a fraction. The software also converts the Detection Time Limit to a Maximum Number of Flashes by the algorithm:

Maximum Number of Flashes=Detection Time Limit×Flash Rate. (25)

The detection system then measures the sample until either the Target Counts or the Maximum Number of Flashes is achieved. For example, if the end user requests a Target Precision of 3% and a Detection Time Limit of 0.100 seconds, and if the Flash Rate is 100 Hertz, the detection system will measure the sample until about 1,100 counts are recorded or until 10 flashes occur, whichever occurs first.

IV.C Example 3

Photoluminescence Polarization Assays Using a Continuous Light Source

This example describes systems for performing, among others, photoluminescence polarization assays using a continuous light source.

The end-user configures the instrument with a Target Polarization Precision (mP) and a Detection Time Limit. The Detection Time Limit allows the user to maintain a minimal throughput, even if the sample has low intensity. In the following Methods, it is assumed that the end user requests a Target Polarization Precision of 3 mP (0.003) and a Detection Time Limit of 0.100 seconds, unless otherwise noted.

IV.C.1 Method 1—Constant Counts

In "Method 1," the detection system software converts the Target Polarization Precision to Target Counts by the algorithm of equation 16, repeated here for clarity:

$$\text{Target Counts} = \frac{1}{2 \times (\text{Target Polarization Precision})^2} \quad (26)$$

Here, Target Polarization Precision is expressed as a fraction (3 mP=0.003). For each polarization state, parallel and perpendicular, the detection system then measures the sample until either the Target Counts (55,600 counts) or the Detection Time Limit (0.100 seconds) is achieved.

This method potentially will integrate the parallel and perpendicular channels for different amounts of time depending on the polarization state of the sample. One requirement this imposes is that the integrated energies (e.g., counts) must be converted to flux (energy per time or intensity) or equivalent to calculate the polarization value properly. If the polarization value of the sample happens to be 0 mP, this method optimally collects the correct number of counts for each channel (as noted above in section III.E.2.d). If the polarization value is greater than 0 mP, the method will collect more than the required minimum number of counts (the precision will be better than the user requested). In worse case scenarios (between 0 and 500 mP), this method will integrate for twice as long as necessary. The method also will have extra difficulty achieving the Target Polarization Precision when the Detection Time Limit is too short. For example, if the Detection Time Limit allows enough time to obtain the Target Counts for the parallel channel, but not for the perpendicular channel, given their relative intensities, this method will integrate less than the total allowed detection time (i.e., two times the Detection Time Limit for serial measurements) and yet not achieve the Target Polarization Precision.

IV.C.2 Method 2—Complete Constant Counts

In "Method 2," the user optionally inputs an Expected Polarization value (e.g., 200 mP), to avoid the extra integration time inherent in worst-case scenarios under the constant counts method. Using the Expected Polarization value, the method can optimally collect counts for that polarization value. The Target Counts algorithm is then equation 15, repeated here for clarity:

$$\text{Target Counts} = \left[ \frac{1 - (\text{Expected Polarization})^2}{\sqrt{2} \times \text{Target Polarization Precision}} \right]^2 \quad (27)$$

Here, the Expected Polarization is expressed as a fraction (200 mP=0.200). The parallel and perpendicular channels are integrated in the same manner as with the constant counts method [i.e., until either the Detection Time Limit (0.100 seconds) or the Target Counts (51,200 counts) is reached]. As an alternative to having the user enter an Expected Polarization parameter, the instrument may quickly pre-read the sample to establish a crude polarization value estimate that can be used instead. As a second alternative the Expected Polarization can be estimated by the partially accumulated parallel and perpendicular intensities (before the termination of the accumulation). Such a dynamic method works best when the parallel and perpendicular intensity values are measured simultaneously.

IV.C.3 Method 3—Constant Time

In "Method 3," the parallel polarization channel is integrated until either a derived Target Counts or a Detection Time Limit is achieved, while the perpendicular channel is integrated until the actual integration time of the parallel channel. The detection system converts the Target Polarization Precision to Target Counts by the algorithm of equation 20, repeated here for clarity:

$$\text{Target Counts} = \frac{16/27}{(\text{Target Polarization Precision})^2} \quad (28)$$

Here, Target Polarization Precision is expressed as a fraction (3 mp=0.003). The parallel channel is integrated until the intensity reaches the Target Counts (65,800 counts) or until the sampling period reaches the Detection Time Limit (0.100 seconds), whichever occurs first, and the actual integration time is recorded (e.g., 0.066 seconds for a flux of 1,000,000 cps). The resulting integration time then is used as the Detection Time Limit for the perpendicular channel. The perpendicular channel then is integrated until the new Detection Time Limit (0.066 seconds).

This method may have one or more advantages. For example, both parallel and perpendicular channels are integrated for the same amount of time, such that the polarization can be calculated directly form the integrated intensities. In addition, two detectors can integrate the parallel and perpendicular intensities simultaneously in an efficient manner. In this case, the signal from the parallel channel detector sets the integration time for both detectors. The constant counts method, for example, would cause the perpendicular channel detector to integrate longer than the parallel detector. Thus, the parallel channel would have extra light that would not be measured.

This method also is relatively efficient. For example, if the polarization value of the sample happens to be 333 mP, this method optimally collects the correct number of counts for each channel (as discussed in section III.E.2.e). If the polarization value is different than 333 mP, the method will collect more than the required minimum number of counts (the precision will be better than the user requested). However, in worse case scenarios (between 0 and 500 mP), this method will only integrate for 9% extra time. This method also behaves well when the Detection Time Limit occurs before the Target Counts.

IV.C.4 Method 4—Complete Constant Time

In "Method 4," to avoid the extra integration time associated with Method 3 (the constant time method) in worse case scenarios, the user optionally may input an Expected Polarization value (e.g., 200 mP), as with Method 2 (the complete constant counts method). Using the Expected Polarization value, the method can optimally collect counts for that polarization value. The Target Counts algorithm is then equation 19, repeated here for clarity:

$$\text{Target Counts} = \frac{[1 - (\text{Expected Polarization})] \times [1 + (\text{Expected Polarization})]^2}{2 \times (\text{Target Polarization Precision})^2} \quad (29)$$

Here, the Expected Polarization is expressed as a fraction (200 mP=0.200). The parallel and perpendicular channels are integrated in the same manner as with the constant time method [i.e., parallel until either the Detection Time Limit (0.100 seconds) or the Target Counts (64,000 counts) is reached, and perpendicular until the actual time of the parallel integration (e.g., 0.064 seconds for a flux of 1,000,000 cps)]. As an alternative to having the user enter an Expected Polarization parameter, the instrument may quickly pre-read the sample to establish a crude polarization value estimate that can be used instead. As a second alternative the Expected Polarization can be estimated by the partially accumulated parallel and perpendicular intensities (before the termination of the accumulation). Such a dynamic method works best when the parallel and perpendicular intensity values are measured simultaneously.

IV.C.5 Method 5—Adjusted Constant Counts

In "Method 5," to avoid the Detection Time Limit difficulties of the constant counts method when measuring the parallel and perpendicular channels serially, the Target Counts is calculated as in the constant counts method The parallel channel is integrated as in the constant counts method, except that the actual integration time is recorded. Any spare time from the parallel channel integration (the time difference between the actual time and the Detection Time Limit) then is added to the Detection Time Limit of the perpendicular channel. For example, with a Detection Time Limit of 0.100 seconds and a Target Polarization Precision of 3 mP, the Target Counts is 51,200 counts. If the parallel channel flux is 1,000,000 cps, then the actual integration time will be 0.051 s. The Detection Time Limit for the perpendicular channel would then be 0.149 s [0.100+(0.100−0.051)]. The complete constant counts method can be adjusted in the same manner.

IV.C.6 Comparison of Methods 1–5

FIGS. 13–16 compare the relative performance of fluorescence polarization methods 1–5. The variables "Const counts 1," "Const counts 2," "Const time," "Comp. Counts 1," and "Comp. Time" refer to the "constant counts," "adjusted constant counts," "constant time," "complete constant counts," and "complete constant time" methods defined above. The intensity in the drawings is the parallel channel intensity. The target error in the drawings refers to the Target Polarization Precision. The performance metric is a method to compare the algorithms that weights the total integration time (parallel channel plus perpendicular channel) and the deviation from Target Polarization Precision for several polarization values (0, 30, 100, 200, 300, 400, 500 mp). The equation for the metric is:

Metric=Sum {(Parallel Time+Perp Time)× (Pol Precision−Target Pol Precision)$^2$} (30)

Here, Parallel Time and Perp Time are the parallel and perpendicular channel actual integration times, respectively, Pol Precision is the resulting polarization precision after applying the methods, and Target Pol Precision is the user input Target Polarization Precision.

IV.D. Example 4

Miscellaneous Performance Evaluations

This example describes selected properties of detection circuitry from the apparatus of FIGS. 3–6.

Figure 17:
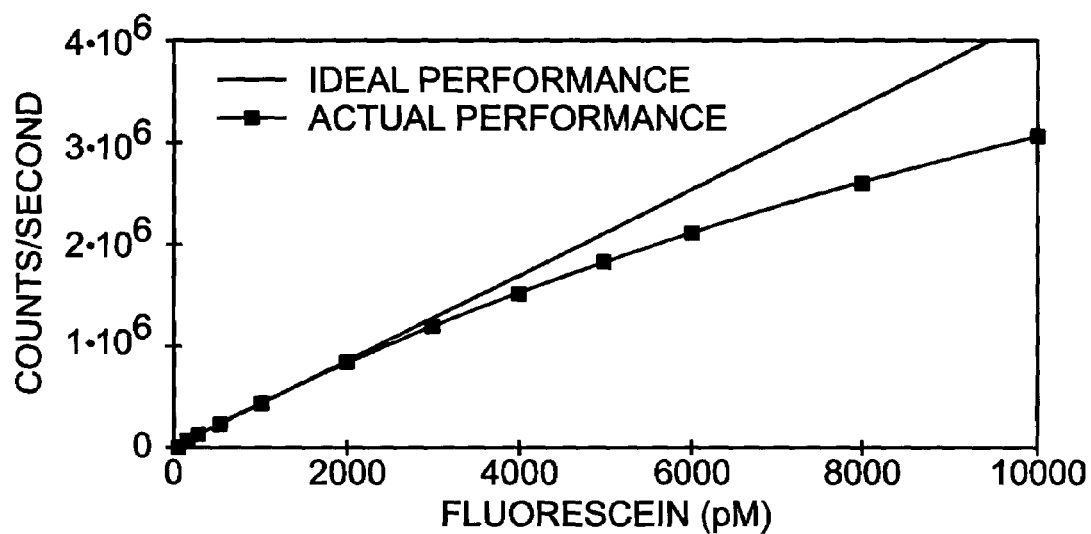
FIGS. 17 and 18 are response curves showing nonlinearity of the digital counting circuit from the apparatus shown in FIGS. 3–6.
Figure 18:
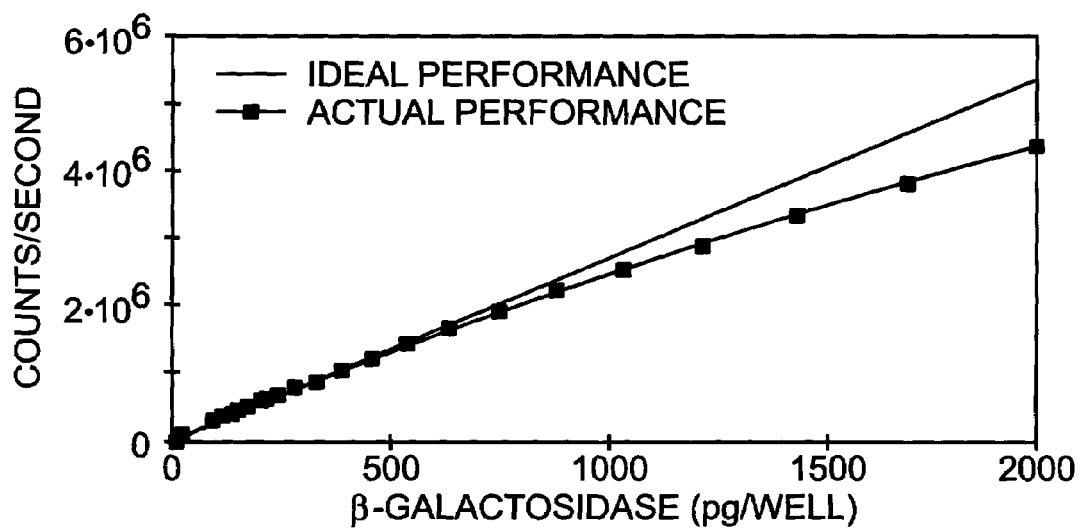

FIGS. 17 and 18 are response curves showing nonlinearity of the digital counting circuit from the apparatus shown in FIGS. 3–6. FIG. 17 was generated using the photoluminescence optical system, and shows a nonlinearity of 10% at 1.5 million counts/second, 15% at 2 million counts/second, 23% at 2.5 million counts/second, and 27% at 3 million counts/second. FIG. 18 was generated using the chemiluminescence optical system, and shows a nonlinearity of 5% at 2 million counts/second, 10% at 3 million counts/second, and 20% at 4 million counts/second.

Figure 19:
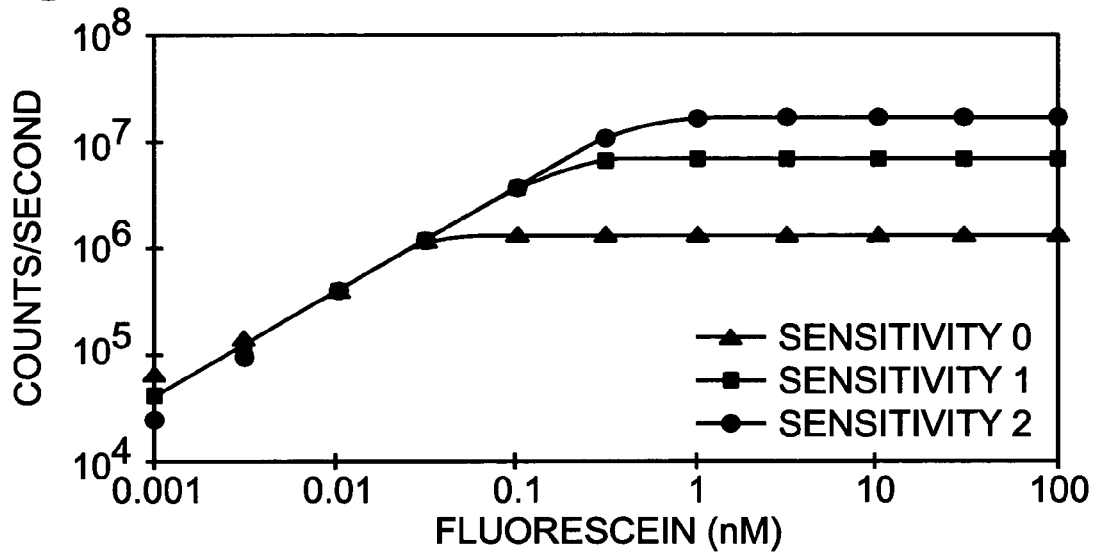
FIG. 19 is a response curve showing saturation of the integrating capacitor in the analog counting circuit from the apparatus shown in FIGS. 3–6.

FIG. 19 is a response curve showing saturation of the integrating capacitor in the analog counting circuit from the apparatus shown in FIGS. 3–6. The curves were generated using a 100-millisecond sampling period. Data are shown for three capacitors, including a relatively large capacitor (sensitivity 0) and a relatively small capacitor (sensitivity 2). The large capacitor saturates at higher light intensities than the small capacitor. The response for the largest capacitor is linear to about 10 million counts/second, which is about tenfold higher than with the digital counting circuit.

Figure 20:
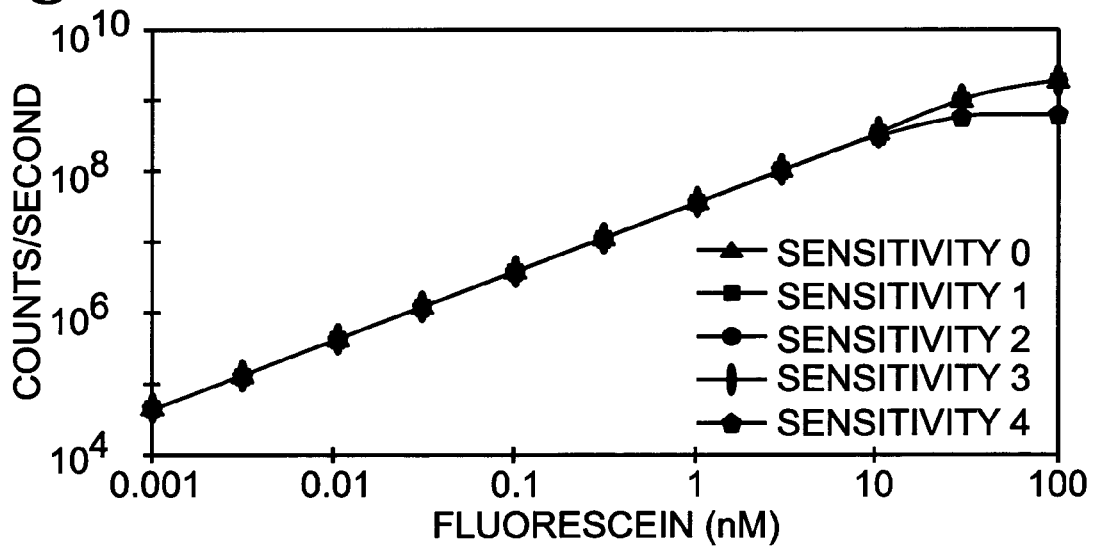
FIG. 20 is a response curve showing saturation of the analog counting circuit when used with the comparator option from the apparatus shown in FIGS. 3–6.

FIG. 20 is a response curve showing saturation of the analog counting circuit when used with the comparator option from the apparatus shown in FIGS. 3–6. Specifically, FIG. 20 was generated using the same apparatus, sample, and 100-millisecond sampling period used in generating FIG. 19. The response is linear to about 1 billion counts/second, at least for the capacitors corresponding to sensitivities 0–3.

Although the invention has been disclosed in preferred forms, the specific embodiments thereof as disclosed and illustrated herein are not to be considered in a limiting sense, because numerous variations are possible. Applicants regard the subject matter of their invention to include all novel and nonobvious combinations and subcombinations of the various elements, features, functions, and/or properties disclosed herein. No single feature, function, element or property of the disclosed embodiments is essential. The following claims define certain combinations and subcombinations of features, functions, elements, and/or properties that are regarded as novel and nonobvious. Other combinations and subcombinations may be claimed through amendment of the present claims or presentation of new claims in this or a related application. Such claims, whether they are broader, narrower, or equal in scope to the original claims, also are regarded as included within the subject matter of applicants' invention.

We claim:

1. A light detection device, comprising:
   a detector configured to receive light from a sample;
   an accumulator configured to generate an accumulator signal corresponding to the total light received by the detector from the sample during a sampling period;
   a timer configured to measure elapsed time during the sampling period; and
   a controller configured to terminate the sampling period after the accumulator signal reaches a predetermined accumulator value or after the elapsed time reaches a predetermined detection time limit, whichever occurs first.

2. The device of claim 1, wherein a target measurement precision is used to calculate the predetermined accumulator value.

3. The device of claim 2, wherein a model of measurement noise further is used to calculate the predetermined accumulator value.

4. The device of claim 3, wherein the model of measurement noise is shot noise.

5. The device of claim 2, wherein an estimated measurement result further is used to calculate the predetermined accumulator value.

6. The device of claim 5, wherein the estimated measurement result is calculated using light received from the sample prior to or during the sampling period.

7. The device of claim 1, wherein the device is configured to receive light automatically and sequentially from a plurality of samples.

8. The device of claim 7, wherein the plurality of samples are disposed at different positions in a microplate or a microarray.

9. The device of claim 7 further comprising an automatic sample handler configured to advance samples for analysis, wherein the time between beginning to analyze successive samples is shorter if the accumulator signal reaches the predetermined accumulator value before the elapsed time reaches the predetermined detection time limit.

10. The device of claim 7, wherein the device is configured to receive light automatically from each of the plurality of samples during first and second sampling periods.

11. The device of claim 7, wherein the predetermined detection time limit is calculated using a user-inputted maximum total time for receiving light from the plurality of samples.

12. The device of claim 1, wherein the device is configured to receive light from the sample automatically during first and second sampling periods.

13. The device of claim 12, wherein the first and second sampling periods are sequential.

14. The device of claim 12, wherein the first and second sampling periods are at least partially overlapping.

15. The device of claim 12, wherein the controller is configured to terminate the first and second sampling periods independently after an accumulator signal for each period reaches a predetermined accumulator value or after the elapsed time for each period reaches a predetermined detection time limit, whichever occurs first.

16. The device of claim 12, wherein the duration of the second sampling period is determined at least in part by the duration of the first sampling period.

17. The device of claim 16, wherein the controller is configured to terminate the second sampling period such that it has at least substantially the same duration as the first sampling period.

18. The device of claim 16, wherein the controller is configured to terminate the second sampling period such that it has a duration equal to about twice the predetermined detection time limit minus the duration of the first sampling period.

19. The device of claim 12, wherein the device is configured such that the light received during the first and second sampling periods is of at least substantially the same wavelength.

20. The device of claim 12, wherein the device is configured such that the light received during the first and second sampling periods is of at least substantially different wavelengths.

21. The device of claim 12, wherein the device is configured such that the light received during the first and second sampling periods is of at least substantially different polarization.

22. The device of claim 12, further comprising a processor configured to compute a quantity related to the polarization of the light received during the first and second sampling periods.

23. The device of claim. 22, wherein the quantity is a luminescence polarization or a luminescence anisotropy.

24. The device of claim 12 further comprising a processor configured to compute a quantity related to resonance energy transfer efficiency in the sample based on the light received during the first and second sampling periods.

25. The device of claim 12 further comprising a processor configured to compute a quantity related to a ratio of the light received during the first and second periods.

26. The device of claim 1 further comprising an excitation source configured to excite emission of light from the sample.

27. The device of claim 26, wherein the excitation source is a light source.

28. The device of claim 26, wherein the excitation source is an electrical potential or current.

29. The device of claim 1, the detector, accumulator, accumulator signal, and sampling period being a first detector, a first accumulator, a first accumulator signal, and a first sampling period, respectively, further comprising:
   a second detector configured to receive light from the sample; and
   a second accumulator configured to generate a second accumulator signal corresponding to the total light received by the second detector from the sample during a second sampling period.

30. The device of claim 1, wherein the accumulator is discrete and generates the accumulator signal by counting pulses from the detector corresponding to quanta of detected light.

31. The device of claim 1, wherein the accumulator is analog and generates the accumulator signal by charging an integration capacitor, the charge on the capacitor corresponding to the amount of detected light.

32. The device of claim 31, the accumulator including a plurality of integration capacitors having substantially different capacities from one other, wherein the amount of detected light required to generate an accumulator signal equal to the predetermined accumulator value is selectable by choosing a particular one of the integration capacitors.

33. The device of claim 31, the accumulator also including a discrete accumulator that accumulates the signal by counting pulses from the detector corresponding to quanta of detected light, wherein the device switches between the discrete and analog accumulators based on the amount of light detected.

34. The device of claim 1, wherein the accumulator is digital and generates the accumulator signal by digitally measuring and summing the output of the detector at a plurality of discrete times during the sampling period.

35. The device of claim 1 further including a plurality of accumulators simultaneously operatively connected in parallel to the detector, each accumulator being configured to generate an integration value proportional to the integrated output of the detector during the sampling period, wherein the proportionality between the accumulator signal and the amount of detected light is substantially different for the different accumulators.

36. The device of claim 1, wherein the detector is selected from a group consisting of photomultiplier tubes, photodiodes, avalanche photodiodes, and charge-coupled devices.

37. The device of claim 1, wherein the device is adapted to switch between digital and analog counting modes, depending on the amount of detected light.

38. The device of claim 1, wherein the predetermined detection time limit is measured by pulses of a flash lamp.

39. A method of detecting light from a sample, comprising:
    detecting photons incident on a detector during a sampling period;
    collecting data representative of the cumulative number of photons detected during the sampling period; and
    terminating the sampling period when the cumulative number of photons detected during the sampling period reaches a predetermined threshold or a predetermined sample time expires, whichever occurs first.

40. The method of claim 39, further comprising calculating the predetermined threshold based on a target measurement precision.

41. The method of claim 39, further comprising repeating the steps of detecting, collecting, and terminating for the same sample.

42. The method of claim 41, further comprising computing a polarization based on the detected light.

43. The method of claim 41, further comprising computing a resonance energy transfer efficiency based on the detected light.

44. The method of claim 41, further comprising computing a ratio based on the detected light.

45. The method of claim 39, further comprising repeating the steps of detecting, collecting, and terminating for a second sample.

46. A light detection device, comprising:
    means for receiving light from a sample;
    means for generating an accumulator signal corresponding to the total light received by the detector from the sample during a sampling period;
    means for measuring elapsed time during the sampling period; and
    means for terminating the sampling period after the accumulator signal reaches a predetermined accumulator value or after the elapsed time reaches a predetermined detection time limit, whichever occurs first.

* * * * *